US010146064B2

(12) United States Patent
Saur et al.

(10) Patent No.: US 10,146,064 B2
(45) Date of Patent: Dec. 4, 2018

(54) APPARATUS AND METHOD FOR ASCERTAINING A TYPE OF SPECTACLE LENS AND APPARATUS AND METHOD FOR DETERMINING A REFRACTIVE POWER DISTRIBUTION OF A PROGRESSIVE SPECTACLE LENS

(71) Applicants: Carl Zeiss Vision International GmbH, Aalen (DE); Carl Zeiss Vision Ireland Ltd., Wexford (IE); Carl Zeiss Vision Inc., San Diego, CA (US)

(72) Inventors: Konrad Saur, Aalen (DE); Paraic Begley, Waterford (IE); Ray Steven Spratt, Petaluma, CA (US); Timo Kratzer, Aalen (DE)

(73) Assignees: Carl Zeiss Vision International GmbH, Aalen (DE); Carl Zeiss Vision Ireland Ltd., Wexford (IE); Carl Zeiss Vision Inc., San Diego, CA (US)

( * ) Notice: Subject to any disclaimer, the term of this patent is extended or adjusted under 35 U.S.C. 154(b) by 0 days.

(21) Appl. No.: 15/843,952

(22) Filed: Dec. 15, 2017

(65) Prior Publication Data

US 2018/0107022 A1 Apr. 19, 2018

Related U.S. Application Data

(60) Division of application No. 14/601,188, filed on Jan. 20, 2015, which is a continuation of application No. PCT/US2013/051529, filed on Jul. 22, 2013.

(Continued)

(30) Foreign Application Priority Data

Jul. 20, 2012 (DE) .................. 10 2012 014 399

(51) Int. Cl.
*G06Q 30/00* (2012.01)
*G02C 7/02* (2006.01)
(Continued)

(52) U.S. Cl.
CPC ............ *G02C 7/027* (2013.01); *A61B 3/0025* (2013.01); *G02C 7/028* (2013.01); *G02C 7/061* (2013.01);
(Continued)

(58) Field of Classification Search
CPC ............ G06Q 30/0663; G06Q 30/0621; A61B 3/0025
(Continued)

(56) References Cited

U.S. PATENT DOCUMENTS 4,989,316 A 2/1991 Logan et al.
5,444,503 A 8/1995 Kelch et al.
(Continued)

OTHER PUBLICATIONS

DIN EN ISO 13666: Nov. 1998 of the DIN Deutschen Institut fuer Normung, e.V., pp. 1 to 51.
(Continued)

*Primary Examiner* — Robert E Tallman
(74) *Attorney, Agent, or Firm* — Walter Ottesen

(57) ABSTRACT

An apparatus is for ascertaining and outputting a type of spectacle lens suitable for a spectacle wearer with a visual characteristics providing device, for providing visual characteristics of the spectacle wearer, a needs providing device, for providing individual needs of the spectacle wearer, a spectacle lens type providing device, for providing a plurality of types of spectacle lenses having predetermined characteristics, a desired characteristics ascertaining device, for ascertaining desired characteristics of a type of spectacle lens using the provided visual characteristics and the provided individual needs of the spectacle wearer, an assigning (Continued)

device, for assigning at least one type of spectacle lens from among the plurality of types of spectacle lenses to the desired characteristics, on the basis of predetermined assignment rules, and a spectacle lens type outputting device, for outputting the at least one assigned type of spectacle lens. A method is for ascertaining and outputting a type of spectacle lens suitable for a spectacle wearer and also a computer program is for carrying out the method.

12 Claims, 9 Drawing Sheets

Related U.S. Application Data

(60) Provisional application No. 61/673,938, filed on Jul. 20, 2012.

(51) Int. Cl.
*A61B 3/00* (2006.01)
*G02C 7/06* (2006.01)
*G06Q 30/06* (2012.01)

(52) U.S. Cl.
CPC ..... *G06Q 30/0621* (2013.01); *G06Q 30/0633* (2013.01)

(58) Field of Classification Search
USPC ................................ 705/26, 27; 351/159.75
See application file for complete search history.

(56) References Cited

U.S. PATENT DOCUMENTS

| | | | |
|---|---|---|---|
| 5,485,399 A | 1/1996 | Saigo et al. |
| 5,971,537 A | 10/1999 | Fukuma et al. |
| 6,089,713 A | 7/2000 | Hof et al. |
| 6,199,983 B1 | 3/2001 | Kato et al. |
| 6,523,443 B1 | 2/2003 | Hof et al. |
| 6,827,443 B2 | 12/2004 | Fisher et al. |
| 6,852,406 B2 | 2/2005 | Marechal et al. |
| 7,287,853 B2 | 10/2007 | Toshima et al. |
| 7,588,480 B2 | 9/2009 | Kuebler |
| 7,744,217 B2 | 6/2010 | Cabeza et al. |
| 7,771,052 B2 | 8/2010 | Kratzer et al. |
| 7,914,148 B2 | 3/2011 | Fisher et al. |
| 7,980,692 B2 | 7/2011 | Fisher et al. |
| 8,011,996 B2 | 9/2011 | Kuebler |
| 8,079,707 B2 | 12/2011 | Cabeza-Guillen et al. |
| 8,333,469 B2 | 12/2012 | Filipovich et al. |
| 8,425,035 B2 | 4/2013 | von Blanckenhagen |
| 8,591,026 B2 | 11/2013 | Conte et al. |
| 8,690,323 B2 | 4/2014 | Hatanaka |
| 9,022,559 B2 | 5/2015 | Suzuki et al. |
| 9,055,890 B2 | 6/2015 | Cabeza-Guillen et al. |
| 2003/0107707 A1 | 6/2003 | Fisher et al. |
| 2005/0122472 A1 | 6/2005 | Fisher et al. |
| 2008/0111969 A1 | 5/2008 | Covarrubias et al. |
| 2010/0026955 A1 | 2/2010 | Fisher et al. |
| 2010/0030570 A1 | 2/2010 | Kratzer et al. |
| 2011/0054927 A1 | 3/2011 | Renna et al. |
| 2011/0267576 A1 | 11/2011 | Kratzer et al. |
| 2013/0090944 A1 | 4/2013 | Kratzer et al. |

OTHER PUBLICATIONS

International Search Report dated Jan. 10, 2014 of international application PCT/US2013/051529.
Written Opinion of the International Searching Authority dated Jan. 10, 2014 of international application PCT/US2013/051529.
Koeppen, Werner, "Konzeption und Entwicklung von Progressivglaesem", DOZ 10/95, Jul. 11, 2007, pp. 1 to 5.
English translation and Office Action of the German Patent Office, dated Feb. 22, 2013 in German patent application 10 2012 014399.0.
International Preliminary Report on Patentability and Written Opinion of the international searching authority dated May 19, 2015 in international patent application PCT/US13/51529.
Office Action of the Chinese Patent Office dated Jun. 3, 2016 in the corresponding Chinese patent application 201380038616.1.
European Search Report of the European Patent Office dated Jun. 20, 2016 in the corresponding European patent application 13819680.3.
Second Office Action of the Chinese Patent Office dated Apr. 5, 2017 in the corresponding Chinese patent application 201380038616.1.
Third Office Action of the Chinese Patent Office dated Sep. 19, 2017 in the corresponding Chinese patent application 201380038616.1.
Resubmittal of Third Office Action of the Chinese Patent Office dated Sep. 19, 2017 in the corresponding Chinese patent application 201380038616.1.
Fourth Office action and translation of the Chinese Patent Office dated Apr. 10, 2018 in the corresponding Chinese patent application 201380038616.1.

APPARATUS AND METHOD FOR ASCERTAINING A TYPE OF SPECTACLE LENS AND APPARATUS AND METHOD FOR DETERMINING A REFRACTIVE POWER DISTRIBUTION OF A PROGRESSIVE SPECTACLE LENS

CROSS REFERENCE TO RELATED APPLICATIONS

This application is a divisional application of application Ser. No. 14/601,188, filed Jan. 20, 2015, which, in turn, is a continuation application of international patent application PCT/US2013/051529, filed Jul. 22, 2013, which designates the United States and claims priority from U.S. Provisional Application No. 61/673,938, filed Jul. 20, 2012, and German patent application 10 2012 014 399.0 filed Jul. 20, 2012. The present continuation application claims priority to each of the above applications and incorporates herein the entire contents thereof by reference.

FIELD OF THE INVENTION

The invention relates to an apparatus and a method for ascertaining and outputting a type of spectacle lens suitable for a spectacle wearer and to a computer program required for operating the apparatus and a computer program required for carrying out the method.

The invention also relates to an apparatus and a method for determining a refractive power distribution of a progressive spectacle lens and to a computer program suitable for operating the apparatus and a computer program suitable for carrying out the method.

BACKGROUND OF THE INVENTION

The range of spectacle lenses offered has become ever greater and more varied in recent years. New materials, production methods, coating and finishing processes enable the manufacturer to offer spectacle lens products that are tailored even more to the individual needs of the customer. The following paragraphs provide a brief overview of the multitude of variants of the products.

While in the past spectacle lenses were predominantly made from mineral glasses, in particular crown glasses (Abbe dispersion number >55) and flint glasses (Abbe dispersion number <50), in the meantime spectacle lenses from a multiplicity of organic materials are available. Typical organic materials are diethylene glycol bisallyl carbonate or allyl diglycol carbonate (ADC), which are sold by the company PPG Industries under the brand name "Columbia Resin 39" or "CR 39", higher refractive thermosetting polymer materials, such as for example the polythiol urethanes sold under the trade names MR-7, MR-8, MR-10 of the company Mitsui Chemicals (the abbreviation "MR" stands here for "Mitsui Resin"), polymethylmethacrylate (abbreviation: PMMA) or polycarbonate.

Enhanced production engineering capabilities, in particular direct machining by so-called Fast Tool Servo turning machines or milling machines, as are described, for example, in U.S. Pat. No. 6,199,983, make it possible to produce usable optical surfaces even with a highly unsymmetrical form. This necessitates no further working steps, or working steps of a short duration with flat polishing tools, as described, for example, in U.S. Pat. No. 7,588,480. As a result, it is possible to adapt the refractive power distribution of the spectacle lens individually to the needs of the wearer.

Thus, for example, U.S. Pat. No. 5,444,503 discloses the production of spectacle lenses for people with presbyopia from semifinished blanks with a progressive front face, the rear face of which is not only produced on the basis of the prescription values, but also is optimized on the basis of individual conditions of use, such as the corneal vertex distance, object ranges, pantoscopic tilt of the frame, form of the frame, bending and slightly different refraction values for the axis and cylinder in the far and near ranges.

U.S. Pat. No. 6,089,713 describes the production of progressive lenses from semifinished blanks with a spherical or rotationally symmetrically aspherical front face, the rear face of which is produced both on the basis of the prescription values and the addition and which is additionally optimized with regard to individual conditions of use, such as the corneal vertex distance, any aniseikonia, the pantoscopic tilt of the frame, form of the frame, the centering, the pupillary distance, special situations of use, (such as for example screen work, car driving, sport, et cetera) as well as different effects for the right and left eyes, with an effect on the compensation for prismatic side-effects.

Werner Köppen describes in the article "Konzeption and Entwicklung von Progressivgläsern [Design and development of progressive lenses], which appeared in the Deutsche Optikerzeitschrift [German opticians' journal], DOZ 10/95 edition, pages 42 to 46, that physiological requirements are taken into consideration in the design of progressive lenses. Attention is drawn in particular to the measurement of the turning of the head and eyes during car driving and the registration of movements of the eyes and head during office work.

U.S. Pat. No. 6,827,443 describes a system and a method for prescribing and/or dispensing spectacle lenses for a wearer. The method comprises the determination of at least individual visual behavioral patterns with regard to the head movement and/or the eye movements of the wearer as well as the processing of these patterns with respect to a predetermined relationship between known head movement and/or eye movement characteristics and available spectacle lenses in such a way that the processing assigns the wearer to a head movement or eye movement category, which can then be used to issue a recommendation for a spectacle lens for the wearer.

U.S. Pat. No. 6,199,983 B1 also describes an individualization of the refractive power distribution of the spectacle lens for the user. Apart from the aforementioned individual conditions of use, it specifies further optimization parameters, such as the convergence of the eyes, the turning of the eyes, the viewing direction and the face form wrap. The special situations of use are specified by this document on the basis of lifestyle, such as hobbies and occupation. Past preferences and habits of the spectacle wearer are also taken into consideration.

U.S. Pat. No. 7,980,692 concerns the prescribing and/or dispensing of ophthalmic lenses, such as progressive lenses, for a wearer. According to U.S. Pat. No. 7,980,692, usage information is obtained from a wearer and entered into a programmed computer. The programmed computer processes the usage information and provides a specially weighted lifestyle score for each of one or more lifestyle score categories, such that each weighted lifestyle score is a function of a predetermined relationship between the corresponding lifestyle score category and at least one spectacle lens design feature. The programmed computer then selects or designs a spectacle lens design using one or more of the weighted lifestyle scores such that the selected or designed spectacle lens has at least one spectacle lens design feature that has been customized individually to the wearer using one or more of the weighted lifestyle scores.

Enhanced and improved methods and devices for determining defective vision, as are described, for example, in U.S. Pat. No. 7,771,052 or U.S. Pat. No. 7,744,217, also allow an individual adaptation of the refractive power distribution of the spectacle lens to the subsequent wearer. Thus, visual defects of a higher order that become noticeable in particular with wide-opened pupils are taken into consideration.

The optical coating of a spectacle lens may comprise an antireflective coating, a reflective coating, a hard coating, a dirt-repelling coating, a coating preventing or reducing fogging and a coating with an antistatic effect. Finally, there are coatings with a polarizing effect and coatings that produce a desired color impression. Each of these coatings may be formed by one or more individual optically transparent layers. Examples can be taken from the documents U.S. Pat. No. 8,591,026, U.S. Pat. No. 6,852,406 and U.S. Pat. No. 8,425,035.

For optometrists and ophthalmic opticians, known as Eye Care Professionals (shortened to ECPs), this great variety of products and configurational possibilities means that it is increasingly unclear what is being offered overall by the manufacturers. It is therefore increasingly more difficult to select from what they offer the optimum spectacle lens for the customer (note: the term glass is used generally and hereinafter as a synonym for the term lens, even though spectacle lenses made of plastic have by now taken the place of lenses made of mineral glasses in large number on the market) and on the other hand to give the customer a clear idea of the differences between the products.

In the past, the suppliers of spectacle lenses have provided electronic price lists with various filtering functions, which makes searching from the great variety easier. Some manufacturers additionally also offer what are known as consulting tools or demonstrators for spectacle lenses, which are intended to present a visual representation, focusing on the product advantages of specific lens types or lens features, for the customer during a sale. Some manufacturers also offer consulting tools for specific lens types (for example individual progressive lenses), in order to determine the ordering parameters of these spectacle lenses.

U.S. Pat. No. 7,914,148 B2 describes a method and a system for simulating an optical effect and/or characteristic of a selected spectacle lens design for a wearer. This involves retrieving simulation data for the selected spectacle lens design, processing it into image data and displaying it to the spectacle wearer with the aid of a head-mounted display to simulate the optical effect and/or characteristics of the selected spectacle lens design.

The solutions available so far on the market only ever cover a partial aspect of the spectacle lens selection. In particular, aids that take into consideration the inclusion of customer needs and the measured values for the eyes in the specific selection of the spectacle lens, and the variants or special features, are not so far available on the market.

SUMMARY OF THE INVENTION

It is an object of the invention to provide an apparatus for ascertaining and outputting a type of spectacle lens suitable for a spectacle wearer, in particular an electronic spectacle configurator in the form of hardware and associated software, which enable the ECP to handle its individual sales transaction electronically.

This object is achieved by an apparatus for ascertaining and outputting a type of spectacle lens suitable for a spectacle wearer, a computer-implemented method and also corresponding software.

The apparatus according to the invention for ascertaining and outputting a type of spectacle lens suitable for a spectacle wearer comprises the following constituent parts:

a visual characteristics providing device, for providing visual characteristics of the spectacle wearer a needs providing device, for providing individual needs of the spectacle wearer a spectacle lens type providing device, for providing a plurality of types of spectacle lenses having predetermined characteristics a desired characteristics ascertaining device, for ascertaining desired characteristics of a type of spectacle lens using the provided visual characteristics and the provided individual needs of the spectacle wearer an assigning device, for assigning at least one type of spectacle lens from among the plurality of types of spectacle lenses to the desired characteristics, on the basis of predetermined assignment rules, to be precise preferably in such a way that the predetermined characteristics thereof are identical to the desired characteristics and/or that the predetermined characteristics thereof come close to the desired characteristics and a spectacle lens type outputting device, for outputting the at least one assigned type of spectacle lens.

The visual characteristics providing device may be a (preferably electronic) memory, or comprise such a memory, in which previously ascertained visual characteristics of the spectacle wearer can be stored or are stored. The ascertained visual characteristics of the spectacle wearer may be permanently stored in the memory. However, it is also possible that the ascertained visual characteristics are only stored in the memory temporarily. Temporary storage is favorable in particular whenever they can be provided again at any time from another (for example remote) data source by way of a data connection.

Visual characteristics are understood here as meaning measurable characteristics that have an influence on the sight of the spectacle wearer. The visual characteristics include, for example for each eye separately, the prescription values of sphere, cylinder, axis and prism, the addition, any aniseikonia, the centering data—such as for example the pupillary distance, the position of the centering point, positional data of the spectacle frame (known among those skilled in the art as "position of wear" or "POW" for short), the form of frame and size of frame —, the corneal vertex distance, the pantoscopic tilt of the frame, the face form angle of the frame and further physiological data such as the convergence of the eyes, the turning of the eyes, any color amblyopia, the preferred viewing direction, the preferred head posture and preferred viewing and/or head movements. A large number of measuring devices, such as for example phoropters, autorefraction measuring devices, wavefront measuring devices, centering data measuring devices, contrast measuring devices, ophthalmometers, keratometers, corneal vertex value measuring devices, for measuring these physical and physiological data (visual characteristics) are on the market.

Alternatively or optionally in addition it is provided that the visual characteristics providing device comprises a visual characteristics inputting device, for inputting the visual characteristics of the spectacle wearer and/or that the visual characteristics providing device has a communication device, in order to receive the visual characteristics from one or more memory devices. The ascertained visual characteristics of the spectacle wearer can accordingly be fed by way of an inputting device, such as for example a keyboard or a microphone, and/or by way of a data interface, such as for example a wire-bound or wireless data network, to which one or more of the measuring devices specified above are connected, or a simple direct data line to corresponding measuring devices, to the visual characteristics providing device for the purpose of being provided.

As already stated above, the visual characteristics of the spectacle wearer are provided according to the invention in particular in the form of measured physical or physiological data, that is, in the form of values of physical or physiological measured variables.

The needs providing device, for providing individual needs of the spectacle wearer, may likewise be a (for example electronic) memory, or comprise such a memory, in which previously ascertained needs of the spectacle wearer can be stored. Needs are understood within the scope of this invention as meaning the request or wish of the spectacle wearer himself or herself to remedy a perceived or actual deficiency in connection with his or her vision. This includes in particular also information concerning his or her pursuits and activities and his or her environmental conditions during which he or she is impaired or believes that he or she is impaired in vision. The individual needs accordingly include the type of occupation and the type of hobbies as well as the duration thereof, the frequency of screen activity, frequency of driving in a car, contact with dirt and dust, frequency of travel, time spent in normal daylight conditions or in artificial light, exposure to the glare of the sun, activities carried out in the twilight and the frequency thereof, special requirements in respect of near vision, surroundings with changing light conditions, et cetera.

The needs of the spectacle wearer are specified according to the invention in particular in the form of one or more visual requirements and a numerical measure of the frequency and/or duration of the occurrence of the respective visual requirement and/or a numerical measure of the subjective and/or objective importance of the respective visual requirement for the spectacle wearer. The numerical measure of the frequency and/or duration of the occurrence of the respective visual requirement and the numerical measure of the subjective and/or objective importance of the respective visual requirement for the spectacle wearer accordingly determine the weighting of the respective visual requirement. In other words, the weighting of the respective visual requirement is a measure of the visual requirement.

The needs providing device may comprise a needs inputting device, for inputting the individual needs of the spectacle wearer. Alternatively or in addition, the needs providing device may have a communication device, in order to receive the visual characteristics from one or more memory devices. In other words, the ascertained individual needs of the spectacle wearer can be made available by way of an inputting device, such as for example a keyboard or a microphone, and/or by way of a data interface, such as for example a wire-bound or wireless data network, to which a corresponding inputting device is connected.

The spectacle lens type providing device, for providing a plurality of types of spectacle lenses having predetermined characteristics, may be a memory, such as for example a compact disc of the manufacturer. It is also possible that the types of spectacle lenses are provided by way of a data interface, such as for example a wire-bound or wireless data network, by a manufacturer or supplier.

Types of spectacle lenses are groups of spectacle lenses into which the manufacturer has divided the spectacle lenses produced by it or the supplier has divided the spectacle lenses supplied by it. Apart from the classification into single-vision, multifocal and progressive lenses, there are inter alia divisions on the basis of the optical effect (for example spherical, astigmatic, et cetera), the design (that is, the distribution of the refractive effect over the spectacle lens), the intended purpose (for example general use, special requirements such as car driving, reading, office, et cetera), the coating (for example with an anti-fog coating, with a dirt-repelling coating, with a scratch protection layer, et cetera) or the filter effect (for example antireflective, polarizing, reflective, tinted, phototropic, et cetera) or else combinations thereof.

A desired characteristics ascertaining device, for ascertaining desired characteristics of a type of spectacle lens using the provided visual characteristics and the provided individual needs of the spectacle wearer may be, for example, a data processing device, which on the basis of a preselected algorithm assigns to specific needs and visual characteristics corresponding desired characteristics for the spectacle lens and consequently the type of spectacle lens.

Desired characteristics of the spectacle lenses are understood as meaning characteristics that the spectacle lens should have on the basis of the provided visual characteristics and the provided individual needs of the spectacle wearer. According to the invention, these characteristics are in particular in the form of characteristics that a spectacle lens can have in principle, and corresponding numerical measures for the need or necessity therefor, in order to enable the spectacle wearer to have the best possible visual impression under the conditions in which he or she usually wears the spectacles. On account of different typing of different manufacturers and suppliers, the characteristics characterizing different types of spectacle lenses may also deviate from one another. However, the use of numerical measures also allows consistent use of characteristics over different types of spectacle lenses, and in particular different classifications of types of spectacle lenses, in that the numerical measures representing a weighting can be chosen to be correspondingly greater or smaller.

The assigning device may also be a data processing device, or it may be the data processing device described in the paragraph above. This is intended and set up for the purpose of ascertaining from the desired characteristics at least one type of spectacle lens from among the plurality of types of spectacle lenses of the manufacturer and or of the supplier of which the predetermined characteristics come closest to, or even correspond to, the requirements profile formed by the desired characteristics. Therefore, the requirements profile should be understood as meaning the entirety of the desired characteristics, that is, all of the characteristics and the associated numerical measures thereof for the need or necessity therefor. This process of assignment, that is, of ascertaining one or more suitable types of spectacle lens(es) from among the entirety of the types of spectacle lenses available is performed on the basis of preselected assignment rules.

The spectacle lens type outputting device, for outputting the at least one assigned type of spectacle lens may be, for example, a screen or a printer. In principle, a loudspeaker, which can output the type of spectacle lens acoustically, also comes into consideration.

Optionally, the apparatus may be equipped with a characteristics outputting device, for outputting the desired characteristics, in order not only to output to the user the type of spectacle lens suitable for the spectacle wearer, but also to indicate which desired characteristics the type of spectacle lens should have if, for example, one takes into consideration the measured refraction values and the indications of the spectacle wearer in respect of his or her needs.

It is favorable in this connection if the spectacle wearer can be given the possibility of changing his or her originally indicated needs or changing the calculated desired characteristics, for example because he or she only realizes on the basis of the desired characteristics displayed to him or her that he or she has overrated certain needs or underrated other needs. On account of the last-mentioned requirement, a desired characteristics inputting device may be provided, for changing the desired characteristics.

It has been found that it is easier for the optician, and equally for the customer, to select the appropriate or suitable type of spectacle lens if not only the desired characteristics, that is, the characteristics that a spectacle lens should have in the view of the manufacturer or the supplier on the basis of the measurements carried out by the optician and the indications by the spectacle wearer of his or her needs, are output but also the characteristics of the type of spectacle lens or the types of spectacle lenses that the manufacturer or the supplier actually has to offer and that comes or come closest to the ideal in the view of the manufacturer or supplier. A characteristics outputting device may therefore also be provided for this case, for outputting the predetermined characteristics of the at least one assigned type of spectacle lens.

This additional information becomes particularly clear for the user of the apparatus according to the invention if the desired characteristics and the predetermined characteristics are displayed in a superposed manner. The invention therefore optionally provides that the characteristics outputting device is set up in such a way that the desired characteristics and the predetermined characteristics can be displayed in a superposed manner.

If it is assumed that each desired characteristic is made up of a characteristic, such as for example reflection protection, scratch protection, variable glare protection, static glare protection, et cetera, and an associated numerical measure of the need or necessity therefor, such as for example "1" for low need, "2" for an average degree of need and "3" for a great necessity, and that each type of spectacle lens is suitable to a certain degree for satisfying each desired characteristic, the desired characteristics and actual characteristics of the types of spectacle lenses can be displayed in a superposed manner, in particular graphically, in a simple way. Thus, for example, a bar of a size representing the need for the respective characteristic and a bar of a size representing the degree to which it is satisfied may be displayed alongside one another for each of the respective characteristics, such as for example reflection protection, scratch protection, variable glare protection, static glare protection, et cetera. If the bar representing the need for the respective characteristic is greater than the bar representing the degree to which the respective characteristic is satisfied by the assigned type of spectacle lens, the assigned type of spectacle lens does not correspond with respect to this characteristic to the desired state that is given by the visual characteristics and the individual needs of the spectacle wearer. If the bar representing the need for the respective characteristic is the same size or smaller than the bar representing the degree to which the respective characteristic is satisfied by the assigned type of spectacle lens, the assigned type of spectacle lens corresponds with regard to this characteristic to the desired state given by the visual characteristics and the individual needs of the spectacle wearer. Apart from a bar representation, grid-like representations, as shown in the following embodiment, or simple indications of numerical measures (that is, non-graphical representations) also come into consideration for example.

Furthermore, according to the invention, the spectacle lens type outputting device may be set up for outputting one or more of the predetermined characteristics and a sales price corresponding to one or more of the predetermined characteristics for the at least one output assigned type of spectacle lens. The customer is thereby shown what costs he or she must expect if his or her future spectacle lens has a specific characteristic. He or she consequently has the possibility of deciding whether to accept the required price for this characteristic, or rather to do without this feature of the spectacle lens. Or it is also possible that the customer can establish that the characteristic did not initially appear especially important to him or her, but he or she is prepared to pay the price demanded.

In order to illustrate to the customer the considerations specified above, a characteristics inputting device may be provided, in order to change the desired characteristics, the output of the spectacle lens type outputting device and the output of the characteristics outputting device changing as a consequence of the change that is input.

In the example described above, it may be provided, for example, to increase or reduce the bar representing the need for the respective characteristic in the manner of a slider. If, for example, the bar representing the need for the "scratch resistance" characteristic is chosen by the user to be greater than the bar representing the degree to which the "scratch resistance" characteristic is satisfied by the assigned type of spectacle lens, another type of spectacle lens with other predetermined characteristics (actual characteristics) is assigned on the basis of the predetermined assignment rules. This type of spectacle lens (presupposing that there is a type of spectacle lens with the corresponding actual characteristic in the delivery program of the manufacturer and/or supplier) will have a degree to which the "scratch resistance" characteristic is satisfied that corresponds at least to the degree of need for the "scratch resistance" characteristic for the spectacle wearer. This is indicated to the user by a correspondingly changed size of the bar that corresponds to the degree to which the "scratch resistance" characteristic is satisfied by the newly assigned type of spectacle lens. Furthermore, the price of the newly assigned type of spectacle lens is displayed to the user, so that the user can see directly what price he or she would have to pay for his or her need for greater scratch resistance.

A spectacle lens type inputting device may also be provided, in order to select one of the output types of spectacle lenses and/or to change at least one of the output types of spectacle lenses. This enables the spectacle wearer to check the influence of the chosen type on the characteristics and compare it with the requirements profile.

It is most particularly advantageous if the apparatus comprises an order placing device, in order to place an order for a spectacle lens.

The corresponding computer-implemented method according to the invention for ascertaining and outputting a type of spectacle lens suitable for a spectacle wearer comprises the following method steps:

providing visual characteristics of the spectacle wearer, in particular in the form of physical and/or physiological measured values providing individual needs of the spectacle wearer, in particular in the form of visual requirements and corresponding weightings providing a plurality of types of spectacle lenses having predetermined characteristics (actual characteristics)

ascertaining desired characteristics of a type of spectacle lens, in particular in the form of characteristics and corresponding numerical measures for the need or necessity therefor using the provided visual characteristics and the provided individual needs of the spectacle wearer assigning at least one type of spectacle lens from among the plurality of types of spectacle lenses to the desired characteristics on the basis of predetermined assignment rules outputting the at least one assigned type of spectacle lens.

In addition, one or more of the following method steps may also be carried out:

measuring the visual characteristics of the spectacle wearer inputting the individual needs of the spectacle wearer outputting the desired characteristics changing the desired characteristics outputting the predetermined characteristics of the at least one assigned type of spectacle lens, the outputting optionally being performed in a manner superposed with the outputting of the desired characteristics outputting a sales price for the output assigned types of spectacle lenses and optionally outputting the predetermined characteristics to the output assigned types of spectacle lenses and in addition optionally a corresponding sales price selecting a type of spectacle lens from among the assigned types of spectacle lenses producing an individual type of spectacle lens, including additions on the basis of the visual requirement of the spectacle wearer changing the predetermined characteristics placing an order.

The control or the operation of the apparatus described above and the implementation of the method specified above may be performed by a computer program stored on a data carrier.

A further object of the invention is to provide an apparatus for determining a refractive power distribution of a progressive spectacle lens that is particularly suitable or individually adapted for a spectacle wearer and to enable this apparatus if required to output manufacturing parameters for the spectacle lens or if required even to produce the latter.

This object involves the provision of a corresponding method for determining a refractive power distribution of a progressive spectacle lens that is particularly suitable or individually adapted for a spectacle wearer.

This object is achieved by an apparatus, a computer-implemented method and also corresponding software.

The apparatus according to the invention for determining a refractive power distribution of a progressive spectacle lens, which has a distance-vision part, a near-vision part and a progression corridor, connecting the distance-vision part and the near-vision part, comprises the following components:

a first providing device, for providing a measure of at least one variable characterizing the refractive power distribution, of a progressive spectacle lens of progressive spectacles worn in the past by the spectacle wearer, a second providing device, for providing information concerning a current visual impression of the spectacle wearer with the progressive spectacles worn in the past, a third providing device, for providing current visual characteristics of the spectacle wearer, a fourth providing device, for providing current individual needs of the spectacle wearer, a determining device, for determining a measure of a to-be-desired change of the provided measure, taking into consideration the provided information concerning the visual impression of the spectacle wearer with the progressive spectacles worn in the past, a calculating device, for calculating the refractive power distribution of the progressive spectacle lens for the spectacle wearer, taking into consideration the provided current visual characteristics of the spectacle wearer and the provided current individual needs of the spectacle wearer and the determined measure of the to-be-desired change in comparison with the provided measure of the at least one variable of the progressive spectacle lens, characterizing the refractive power distribution, of the progressive spectacles worn in the past by the spectacle wearer.

According to the invention, it is provided that at least one of the at least one variable characterizing the refractive power distribution originates from the group comprising i) width of the distance zone, ii) width of the near zone, iii) gradient of power along the distance zone boundary, iv) gradient of power along the near zone boundary, v) near zone inset, vi) length of and distribution of dioptric power along the progression corridor and vii) astigmatic error distribution outside the distance zone, near zone and progression corridor.

The distance-vision part should be understood in accordance with DIN EN ISO 13666:1998, subclause 14.1.1, as meaning the part of a multifocal or progressive spectacle lens that has the dioptric power for seeing into the distance. According to DIN EN ISO 13666:1998, subclause 14.1.3, the near-vision part or reading part of a multifocal or progressive spectacle lens has the dioptric power for seeing at close quarters. The progression corridor is, according to DIN EN ISO 13666:1998, subclause 14.1.25, the region of a progressive spectacle lens that makes clear vision possible for distances that lie between the distance and close quarters. Near zone inset is understood in accordance with subclause 14.2.8 of the standard DIN EN ISO 13666:1998 as meaning the nasal displacement of the near-vision design reference point with respect to the distance-vision reference point, 5.14 of this standard stipulating that the near-vision design reference point is the point on the front face of a finished spectacle lens or the finished face of a spectacle lens semifinished product at which, according to the manufacturer, the desired design values for the near-vision part exist and subclause 5.15 of this standard stipulating that the distance-vision reference point or main reference point is the point on the front face of a spectacle lens at which the dioptric power for the distance-vision part must be achieved.

Information concerning a current visual impression of the spectacle wearer with the progressive spectacles worn in the past, that is, the visual impression at the current point in time with the old spectacles, constitutes, for example, impressions of the quality of the visual impression with the old progressive spectacles under different visual requirements, such as for example when driving a car, watching TV, working at a screen, reading, cycling, at night, et cetera.

The information concerning the current visual impression of the spectacle wearer with the progressive spectacles worn in the past comprises, for example, at least one individual visual requirement and a corresponding measure of the quality of the visual impression in connection with the at least one individual visual requirement. The measure may be expressed, for example, by way of an actual numerical measure. However, it is also possible to relate different visual requirements to one another. A relative reference is obtained, for example, by the statement "I see well with the old spectacles when driving in daylight conditions but not so well in the dark".

Information concerning the current visual impression of the spectacle wearer with the progressive spectacles worn in the past may also be a measure of the frequency of the at least one individual visual requirement. The spectacle wearer may, for example, state that he or she often uses the spectacles for watching TV, but less for reading.

Current visual characteristics of the spectacle wearer are, according to the above definition, characteristics currently pertaining to the spectacle wearer in the form of physical and or physiological measured values that have an influence on the vision of the spectacle wearer. These include, for example, recently determined prescription values (sphere, cylinder, axis, prism, base), addition, aniseikonia, centering data, such as for example pupillary distance, position of the centering point, positional data of the spectacle frame, form of frame and size of frame, corneal vertex distance, pantoscopic tilt of the frame, face form wrap of the frame, et cetera.

Current individual needs are wishes currently pertaining to the spectacle wearer with respect to vision (see definition above) that he or she would like to be satisfied as far as possible with the new spectacles, and also preselected or desired conditions of use in which the spectacle wearer would like to be able to see as well as possible. The individual needs accordingly include the type of vocational occupation, the frequency of screen activity or driving in a car, et cetera.

The needs of the spectacle wearer are specified according to the invention, for example, in the form of one or more visual requirements and a numerical measure of the frequency and/or duration of the occurrence of the respective visual requirement and/or a numerical measure of the subjective and/or objective importance of the respective visual requirement for the spectacle wearer. The numerical measure of the frequency and/or duration of the occurrence of the respective visual requirement and the numerical measure of the subjective and/or objective importance of the respective visual requirement for the spectacle wearer accordingly determine the weighting of the respective visual requirement. In other words, the weighting of the respective visual requirement is a measure of the visual requirement.

Determining a measure of a to-be-desired change of the provided measure, taking into consideration the provided information concerning the current visual impression of the spectacle wearer with the progressive spectacles worn in the past, means, for example, determining a measure, in particular a value, by which the width of the near-vision part should be increased in order to obtain an improvement in the visual impression with the new progressive lens in comparison with the current visual impression with the old progressive lens worn in the past.

The first, second, third and/or fourth providing device may be one or more (for example electronic) memory or memories, in which the previously ascertained information is stored in the form of data. It is also possible that one or more of the providing devices is or are or comprises or comprise input keyboards, microphones, (wire-bound or wireless) data interfaces with other electronic (measuring) devices or the like.

The apparatus according to the invention may have an outputting device, for outputting the calculated refractive power distribution. Coming into consideration, for example, as the outputting device are a screen, a printer, a loudspeaker, a (wire-bound or wireless) data interface to a possibly more remote device or the like.

The calculating device may be, for example, a processor.

The apparatus may comprise a calculating device, for calculating a path of movement of a working tool, in particular a cutting tool, for producing a geometrical form of at least one face of the progressive spectacle lens to achieve the calculated refractive power distribution of the spectacle lens. The calculating device is accordingly provided for the purpose of, for example, generating the control data for the working tool of a machine described in U.S. Pat. No. 6,199,983 or U.S. Pat. No. 4,989,315. Since the location of the calculation of the design of a progressive spectacle lens adapted to the later user is nowadays often far away from the location of the production of the spectacle lens, the provision of the control data is performed with preference by way of a corresponding outputting device, in particular a (wire-bound or wireless) data interface. However, it is also possible in principle to provide a system comprising a device for determining a refractive power distribution of a progressive spectacle lens of the type described above and a production device, in particular a shaping machine, for example of the type described in U.S. Pat. No. 6,199,983 or U.S. Pat. No. 4,989,315.

The computer-implemented method according to the invention, corresponding to the apparatus according to the invention described above, for determining a refractive power distribution of a progressive spectacle lens with a distance-vision part, a near-vision part and a progression corridor, connecting the distance-vision part and the near-vision part, for a spectacle wearer comprises the following method steps:

providing a measure of at least one variable, characterizing the refractive power distribution, of a progressive spectacle lens of progressive spectacles worn in the past by the spectacle wearer, at least one of the at least one variable originating from the i) group comprising extent of the distance-vision part, ii) extent of the near-vision part, iii) gradient of power along the distance zone boundary, iv) gradient of effect at a boundary between the near-vision part and the progression corridor, v) near zone inset, vi) type of a profile of dioptric power along the progression corridor or length of and distribution of dioptric power along the progression corridor and vii) fingerprint of a peripheral astigmatic error distribution or peripheral astigmatic error distribution outside the distance zone, near zone and progression corridor providing information concerning a current visual impression of the spectacle wearer with the progressive spectacles worn in the past providing current visual characteristics of the spectacle wearer providing current individual needs of the spectacle wearer determining a measure of a change of the measure of the at least one provided variable, characterizing the refractive power distribution, of the progressive spectacle lens of the progressive spectacles worn in the past by the spectacle wearer, taking into consideration the provided information concerning the current visual impression of the spectacle wearer with the progressive spectacles worn in the past calculating the refractive power distribution of the progressive spectacle lens for the spectacle wearer, taking into consideration the provided current visual characteristics of the spectacle wearer and the provided current individual needs of the spectacle wearer and the determined measure of the change of the provided measure of the at least one variable, characterizing the refractive power distribution, of the progressive spectacle lens of the progressive spectacles worn in the past by the spectacle wearer.

A corresponding method according to the invention for producing a progressive spectacle lens comprises the steps of:

providing a refractive power distribution of the progressive spectacle lens determined by the method described above or determining a refractive power distribution of the progressive spectacle lens by the method described above, producing the progressive spectacle lens with the determined refractive power distribution.

The method according to the invention for determining a refractive power distribution of a progressive spectacle lens or the method according to the invention for producing a progressive spectacle lens may also comprise the following method steps:

providing further objective data on the progressive spectacle lens of the progressive spectacles worn in the past by the spectacle wearer, in particular from the group comprising make, product name, material, coating, working, prescription values, the form and size of frame receiving the spectacle lens, individual parameters and special features.

taking into consideration the further objective data in the calculation of the refractive power distribution.

The information concerning the current visual impression of the spectacle wearer with the "old" progressive spectacles worn in the past may comprise at least one individual visual requirement and a corresponding measure of the quality of the visual impression in connection with the at least one individual visual requirement.

The information concerning the current visual impression of the spectacle wearer with the "old" progressive spectacles worn in the past may comprise a measure of the frequency of the at least one individual visual requirement.

The control or the operation of the apparatus described above, for determining a refractive power distribution of a progressive spectacle lens, and the implementation of the method specified above, for determining a refractive power distribution of a progressive spectacle lens or for producing a progressive spectacle lens, may be performed by means of a computer program with a program code when the program is run in a computer.

The computer program may be stored on a machine-readable carrier.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
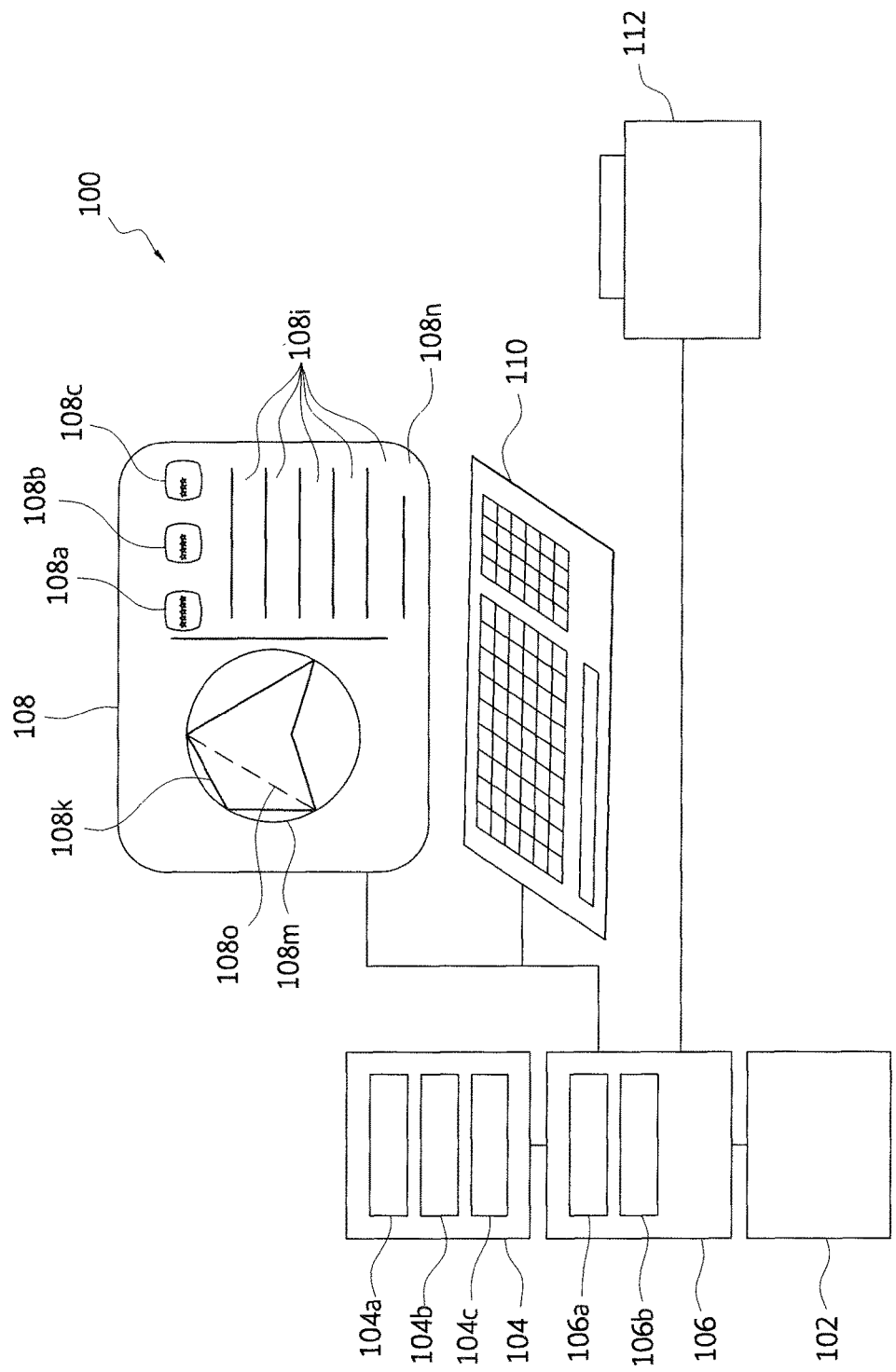
FIG. 1 shows a schematic representation of a spectacle configurator according to the invention.

FIG. 1 shows a schematic representation of an electronic spectacle configurator 100 according to the invention. The spectacle configurator 100 comprises a program memory 102, a data memory 104, a data processing unit 106, a screen 108, a keyboard 110 and a printer 112.

Constituent parts of the data memory 104 are a first memory 104a, in which visual characteristics of the spectacle wearer are stored, a second memory 104b, in which individual needs of the spectacle wearer are stored, and a third memory 104c, in which a plurality of types of spectacle lenses having predetermined characteristics are stored.

In the program memory 102, a computer program is stored, in order to operate the electronic spectacle configurator 100.

The data processing unit 106 is designed and set up for ascertaining desired characteristics of a type of spectacle lens using the visual characteristics provided in the first memory 104a and the individual needs of a spectacle wearer provided in the second memory 104b. The corresponding computing unit is identified in FIG. 1 by the reference sign 106a. The data processing unit 106 is also designed and set up for the purpose of assigning to these desired characteristics at least one type of spectacle lens from among the plurality of types of spectacle lenses stored in the third memory 104c, for a recommendation. The corresponding computing unit is identified in FIG. 1 by the reference sign 106b. The assignment takes place on the basis of specific assignment rules that are presented below by way of example with reference to FIG. 4. The assignment rules are established such that specifically the stored type of spectacle lens of which the predetermined characteristics are identical to the ascertained desired characteristics is assigned. Alternatively or in addition, the assignment rules may be established such that one or more types of spectacle lens(es) of which the predetermined characteristics come close to the desired characteristics is or are assigned.

The screen 108 and the printer 112 may serve independently of one another as spectacle lens type outputting devices, for outputting the at least one assigned type of spectacle lens. In the present case, the screen 108 shows three different types of spectacle lenses (108*a*, 108*b*, 108*c*).

The screen 108, and possibly the printer 112, also serve for outputting the desired characteristics 108*k* and for outputting the predetermined characteristics 108*o* of the at least one assigned type of spectacle lens 108*a*. In the present embodiment, the desired characteristics 108*k* and the predetermined characteristics 108*o* of the assigned type of spectacle lens 108*a* are displayed in a superposed manner in a grid diagram 108*m*. Details of this are explained below with reference to FIGS. 5, 6A and 6B.

Finally, the screen 108 and the printer 112 serve for outputting one or more predetermined characteristics and a price, corresponding to the one or more of the predetermined characteristics, of the at least one output assigned type of spectacle lens. In the present embodiment, a table 108*n* with three columns and six rows is depicted on the screen 108. In the first row of the table 108*n*, the three different types of spectacle lenses (108*a*, 108*b*, 108*c*) are displayed. In the rows lying thereunder, five assigned characteristics 108*i* and the price thereof are respectively entered (cf. also FIGS. 6A and 6B).

The keyboard 110 allows the inputting of the visual characteristics of the spectacle wearer, the inputting of the individual needs of the spectacle wearer, a change of the desired characteristics 108*k*, a change of the predetermined characteristics 108*i* and also the selection of an output type of spectacle lens (108*a*, 108*b*, 108*c*) or else possibly the change of an output type of spectacle lens (108*a*, 108*b*, 108*c*), and finally in this respect allows an order for a spectacle lens to be issued.

An electronic spectacle configurator 100, such as that schematically represented in FIG. 1, may be a constituent part of a system comprising additional electronic devices and information units.

Figure 2:
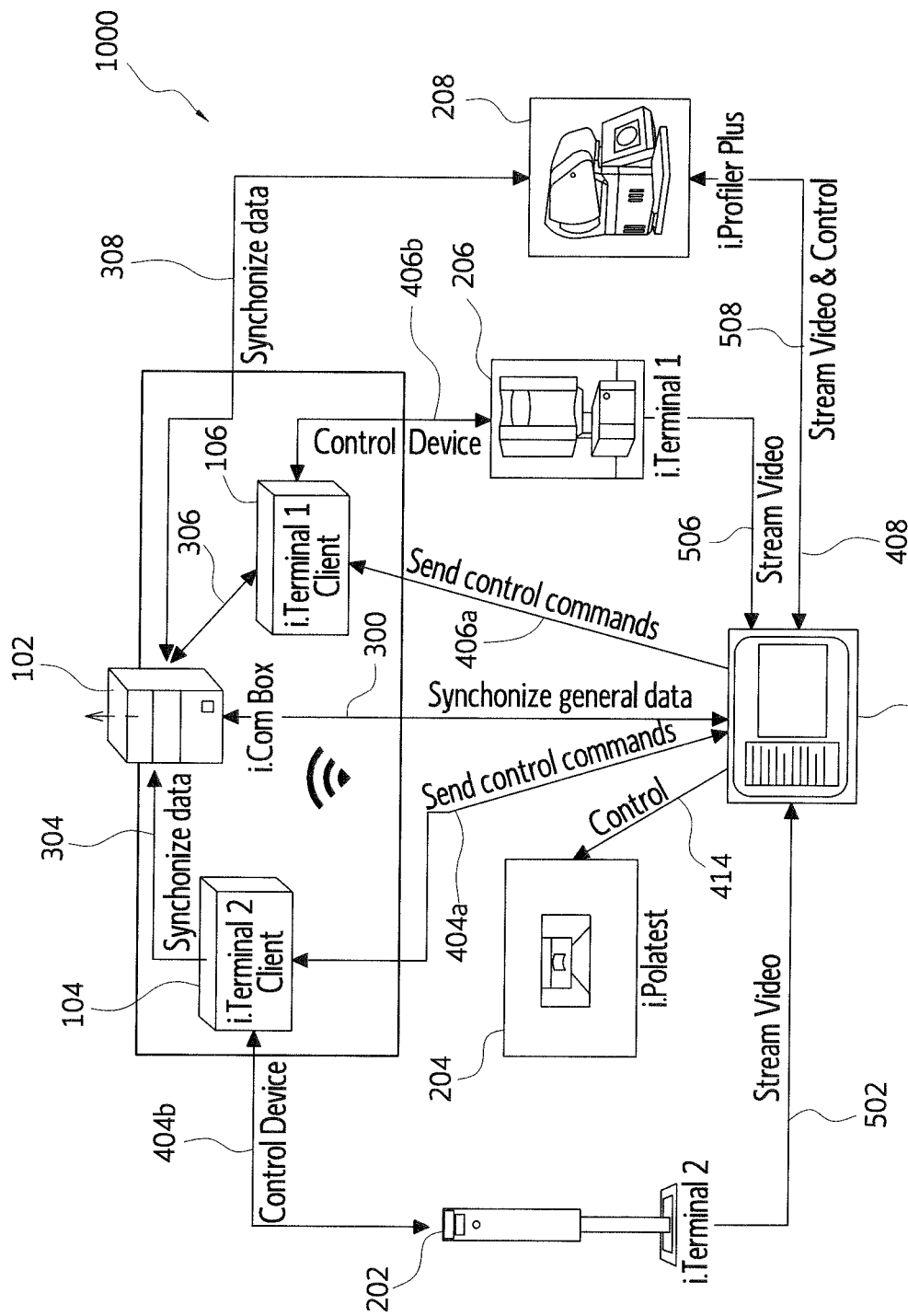
FIG. 2 shows the spectacle configurator that is shown in FIG. 1, incorporated in a data network, together with devices connected to the data network.

FIG. 2 shows the incorporation of an electronic spectacle configurator 100 in such a system 1000.

This system 1000 is formed in the manner of a network comprising a plurality of data processing systems with peripheral devices that are connected to one another by way of data connections. The system 1000 comprises the spectacle configurator 100, a server 102 (known as the i.Com box), a number of clients (104, 106 (the i.Terminal1 and 2 Clients), 100, 208) and a number of measuring devices (202, 204, 206, 208).

The server 102 is set up for the entire data keeping, the control and connection of the measuring devices (202, 204, 206, 208) and the control of the clients (100, 104, 106, 208), which also includes the spectacle configurator 100 and the measuring device 208. The server 102 may be made available either locally at the ophthalmic optician's, centrally at the manufacturer's or as what is known as a Cloud service.

The embodiment that is shown in FIG. 2 shows four measuring devices (202, 204, 206, 208), to be specific the i.Polatest 204, the i.Terminal1 206, the i.Terminal2 202 and the i.ProfilerPlus 208. The i.Polatest 204 is a vision testing device for spectacle lens determination. With this vision testing device, the various aspects of vision, such as visual acuity, spatial vision, interaction of the eyes, et cetera, are accurately analyzed. The i.Terminal1 206 and the i.Terminal2 202 are centering data measuring devices. These serve the purpose of determining data as to how the spectacle lens is to be fitted into the frame selected by the spectacle wearer. The i.ProfilerPlus 208 is a refraction determining device, which combines four functions, to be specific that of an autorefractometer, keratometer, corneal topography system and wavefront-based aberrometer.

While the i.Polatest 204, the i.ProfilerPlus 208 and the i.Terminal2 202 can be activated directly by way of the spectacle lens configurator 100 configured as a tablet computer, that is, in the form of a portable, flat computer, in a particularly lightweight configuration with a touchscreen display, the i.Terminal1 206 requires additional client computers (104, 106), by way of which they can be monitored.

The frontend software (for the clients 100, 104, 106, 208) is available to the ophthalmic optician on one or more personal computers (204, 106, 208) or mobile devices 100 (as a local application or as a server or browser application). All of the clients (100, 104, 106, 208) are connected to the server 102 by way of synchronized data connections (300, 304, 306, 308). Furthermore, there are control connections (414, 404*a*, 404*b*, 406*a*, 406*b*, 408) between the spectacle lens configurator 100 to the measuring devices (202, 204, 206, 208) and also data connections (502, 506, 508) for the transfer of video signals and measurement data from the measuring devices (202, 204, 206, 208) to the spectacle lens configurator 100. All of the connections (300, 304, 306, 308, 414, 404*a*, 404*b*, 406*a*, 406*b*, 408, 502, 506, 508) are configured as wireless connections (radio, infrared or the like). However, it is possible to configure some or all of the connections as lines (wire, fiber-optic or the like).

The client software is of a modular construction, so that the individual components of the spectacle consultation (hereinafter also referred to as steps) can be configured by the ophthalmic optician on the basis of his or her needs. This modular construction is shown on the basis of the schematic representation of a customer consultation or sales discussion with an optician as shown in FIG. 3.

Figure 3:
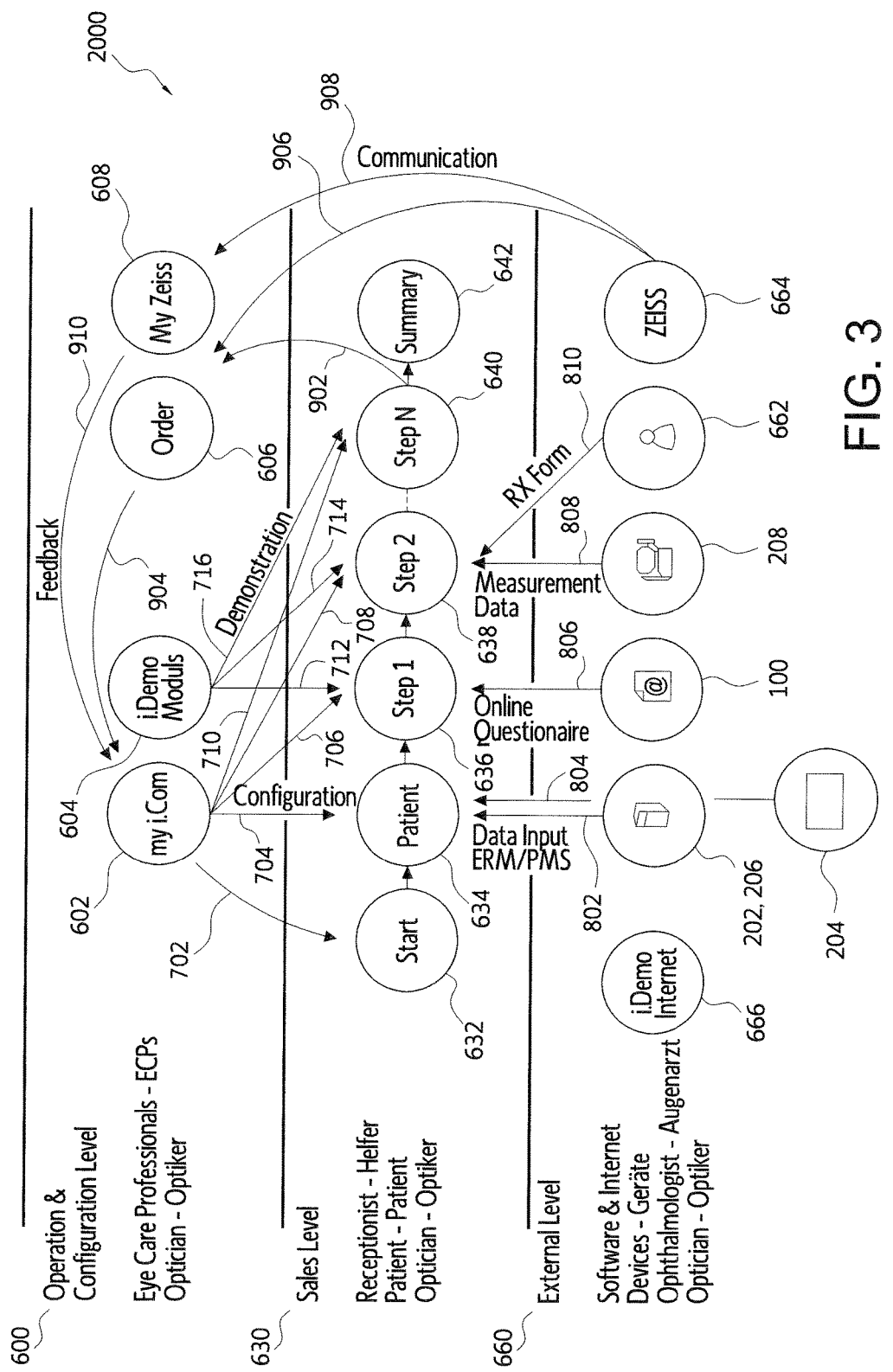
FIG. 3 shows a schematic representation of a customer consultation or a sales discussion with an optician along with the devices involved.

The schematic drawing 2000 as shown in FIG. 3 is subdivided into three levels. The uppermost level is referred to hereinafter as the operation and configuration level 600. The middle level is the sales level 630 and the lower level is the external level 660.

On the operation and configuration level 600, all of the components that concern the operation and configuration of the system 1000 as shown in FIG. 2 are entered, that is, the settings for the operating system software and all of the overarching software modules that do not have anything directly to do with the sales process. In the present embodiment, these are the modules my i.Com 602, i.Demo 604, Order 606 and my Zeiss 608.

My i.Com 602 is the module for the basic settings of the operating system and the client software.

The i.Demo 604 comprises the modules for the demonstration of product advantages of spectacle lenses and finishes, which are partly supported by image and video.

The Order 606 module is software that allows an order for a spectacle lens to be placed.

Combined under my Zeiss 608 are all of the computer programs with which the ophthalmic optician can access the manufacturer's current information directly (online) or can load up-to-date versions of the software. Optionally, the manufacturer may also actively send information to the server or the client software (News Ticker).

On the external level 660, all of the externally connected devices or software modules are entered, in particular the measuring devices (202, 204, 206, 208), mentioned in FIG. 2, and the associated software as well as other aids for ascertaining information concerning the person, and in particular the defective vision, of the spectacle wearer, as far as this is available. Apart from i.Polatest 204, i.Terminal1 206, i.Terminal2 202 and i.ProfilerPlus 208, also to be entered in the diagram 2000 as constituent parts of the external level 660 are accordingly external software modules 202, such as PMS (practice management systems) or EMR (electronic medical records), and the online results enquiry of needs of the spectacle wearer, a phoropter 662 for carrying out a subjective refraction, as well as further future devices or software modules (ZEISS 664), and an Internet access 666.

On the sales level 630, the typical steps (632, 634, 636, 638, 640, 642) of a sales discussion are outlined. It is illustrated by arrows (702, 704, 706, 708, 710, 712, 714, 716), extending from the software modules (602, 604, 606, 608) and pointing to the steps (632, 634, 636, 638, 640, 642), represented as circles, that data and information are exchanged between the sales level and the operation and configuration level, or the user can at any time change between the levels. It is illustrated by the arrows (802, 804, 806, 808, 810) extending from the modules (202, 204, 206, 100, 208, 662, 664) and pointing to the steps (632, 634, 636, 638, 640, 642) that information is required by the external modules (202, 204, 206, 100, 208, 662, 664) for carrying out the steps (632, 634, 636, 638, 640, 642).

The arrows (902, 904, 906) mean that the spectacle lens ordering module can be retrieved from various modules and levels or ordering data can be stored there.

The arrows (908, 910) mean that current manufacturer information, such as price lists or new product information, is available on various levels and in various modules or is stored and accessible there.

In principle, the individual steps (632, 634, 636, 638, 640, 642) of the consultation take the form of individual modules that perform a task defined for this working step (for example customer data—need analysis—eyeglass determination and eye measurement—lens advice—frame selection—centering data acquisition—ordering). The number of modules (632, 634, 636, 638 640, 642) and the function thereof is variable and can be increased or reduced. In principle, it is possible in each of the steps (632, 634, 636, 638, 640, 642) to access the external level, that is, the aforementioned measuring devices, tracers or other external hardware and software.

A sales discussion with the steps outlined in FIG. 3, Start 632, Patient 634, Step 1 632, Step 2 638, . . . Step N 640 and Summary 642, is presented by way of example below with reference to FIGS. 4 to 6:

In the step "Start" 632, the logging on and authentication of the user takes place. Similarly, it is possible to assign different roles and rights to various users.

In the step "Patient" 634, customers can manage master data. Here, a new customer is created or an existing customer is loaded with his or her data for the sales process. Customer data may also be imported from external software or databases. All of the customer-specific measurement data from the external level, such as i.Polatest 204, i.Terminal1 206, i.Terminal2 202, et cetera, are assigned to the customer.

The step "Step 1" 632 represents the need analysis. Here, the ophthalmic optician asks the spectacle wearer questions. The questions concern his or her viewing habits, working environment, leisure activities and use of the spectacles. Each of these questions is aimed at one or more visual requirements of the spectacle wearer (for example screen vision, night-time vision). The answers of the spectacle wearer are categorized and weighted.

Figure 4:
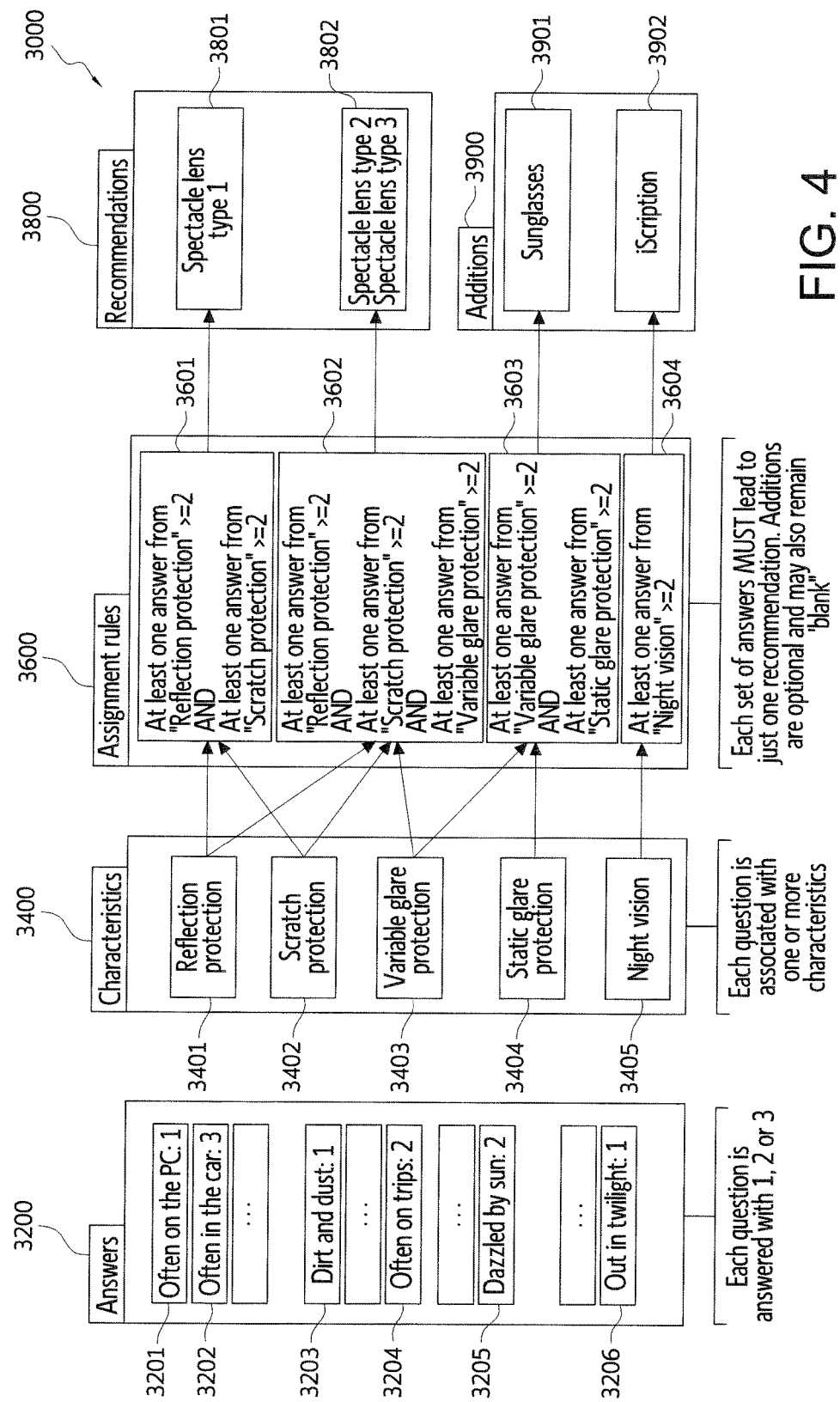
FIG. 4 shows a schematic representation of the concept for the spectacle lens consultation that is based on the electronic spectacle configurator that is shown in FIG. 1.

FIG. 4 shows a diagram 3000, which graphically reveals how a recommendation (3800, 3900) for the future spectacle lenses of the spectacle wearer and any additions is derived from the answers 3200 of the spectacle wearer according to the invention concerning his or her needs (visual requirements). The answers 3200 are entered in the first column of the diagram 3000. The customer indicates in each case with the answer the frequency with which he or she is confronted with this visual requirement. This may take place as in diagram 3000 in 3 stages, from 3=often to 1=never. The scaling may optionally also be refined, for example into ten stages. It is similarly possible also to indicate additionally the frequency of the visual requirement and a weighting thereof. Each individual answer (3201, 3202, 3203, 3204, 3205, 3206) is weighted by a natural number, as in the example from 1 to 3. "3" accordingly means a high weighting, "2" a moderate weighting and "1" a low weighting.

In the step "Step 2" 638, a refraction measurement is carried out. In the present embodiment, both an objective refraction takes place, with the i.ProfilerPlus 208, and a subjective refraction takes place, with a phoropter 662. Here, in a way similar to in the case of the step "Step 1—Patient", the measurement data of the devices can be enquired and these devices can be controlled.

In the step "Step 3", an individual, weighted visual requirements profile of the spectacle wearer is created on the basis of the answers given in the need analysis (Step 1—636) and the measured values of the eyes ascertained in the steps "Patient" 634 and "Step 2" 638. created to the future type of spectacle lens and possible additions. Each of these visual requirements can be linked or satisfied with specific characteristics of spectacle lenses and the additions thereof. As a result, a direct assignment of visual requirements of the spectacle wearer to characteristics of spectacle lenses and the additions thereof is produced.

FIG. 4 shows in the second column a selection of characteristics 3400, which a spectacle lens and the additions thereof may have in a more or less pronounced way. "Reflex protection" 3401, "Scratch protection" 3402, "Variable glare protection" 3403, "Static glare protection" 3404 and also "Night vision" 3405 are mentioned there by way of example. This list may be extended as desired, for example by adding "Optical characteristics", "Solar protection", et cetera.

The desired characteristics are then determined in the manner of relative variables from the weighted answers 3200 of the need analysis and the aforementioned measured values from the steps "Patient" 634 and "Step 2" 638. In the present case, this is performed with the aid of the numerical measures 1, 2 and 3. A numerical measure "3" for the characteristic "Reflection protection" accordingly means the desired characteristic of "High reflection protection required". A numerical measure of "1" for the characteristic "Reflection protection" accordingly means the desired characteristic "No reflection protection required". A numerical measure of "2" for the characteristic "Reflection protection" accordingly means the desired characteristic "There are moderate requirements for reflection protection".

Figure 5:
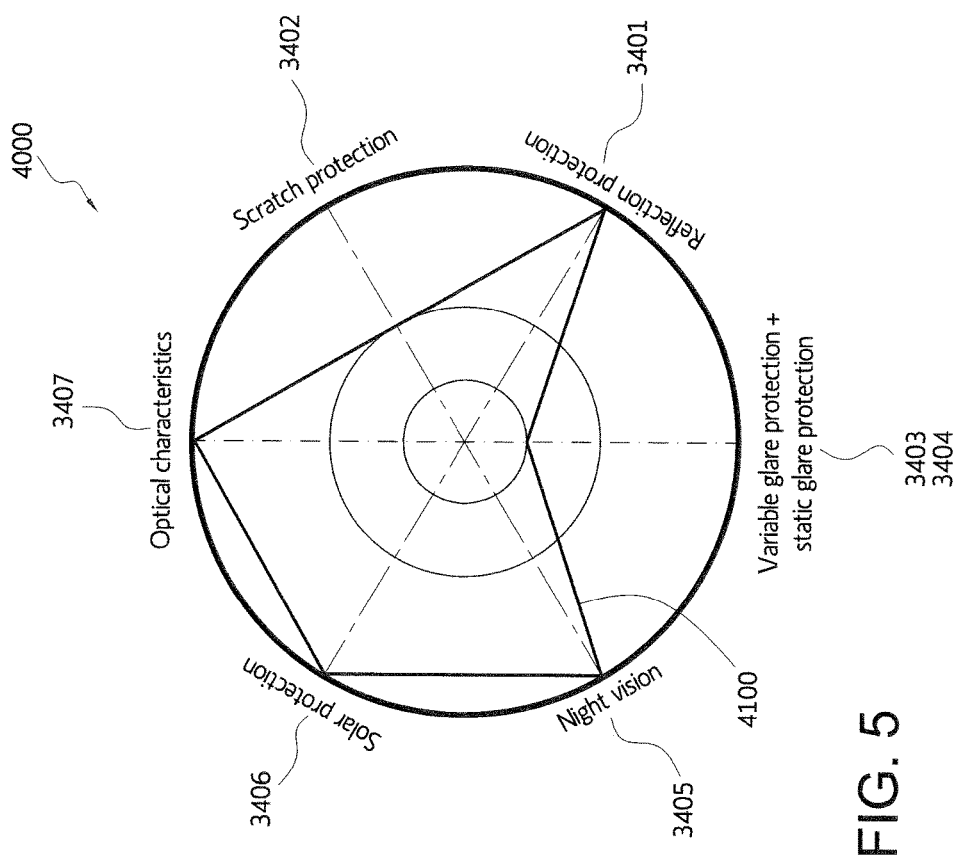
FIG. 5 shows a graphic representation of a requirements profile for a type of spectacle lens, that is, of desired characteristics that the type of spectacle lens should satisfy, in the form of a grid diagram.

In the step "Step 4", this individual visual requirements profile of the spectacle wearer is displayed on the screen 108 of the spectacle lens configurator 100. FIG. 5 shows by way of example the display of the individual requirements profile 4000 in the form of a grid diagram. Alternatively, a display may also take place in the form of a bar diagram, some other graphic or in a numerical form. The grid diagram indicates by circles of different sizes the different numerical measures 1 to 3 of the six characteristics shown at six corners, "Reflection protection" 3401, "Scratch protection" 3402, "Variable glare protection" 3403, "Static glare protection" 3404, "Night vision" 3405, "Solar protection" 3406 and "Optical characteristics" 3407. In the case of the embodiment shown in FIG. 5, the numerical measures are in each case "3" for the desired characteristics 4100 of "Reflection protection", "Night vision" 3405, "Solar protection" 3406 and "Optical characteristics" 3407, "2" for "Scratch protection" and "1" for "Glare protection".

With the aid of previously established assignment rules 3600, of which FIG. 4 shows four by way of example, to be specific the assignment rules (3601, 3602, 3603, 3604), those types of spectacle lenses and the additions thereof that satisfy the desired characteristics according to the visual requirements profile, and come into consideration for a recommendation 3800, are then determined in "Step 5".

On the basis of the assignment rule 3601, there is according to the embodiment precisely one type of spectacle lens with additions that best satisfies the requirements profile, to be specific "Spectacle lens type 1" (recommendation 3801). On the basis of the assignment rule 3602, there are according to the embodiment two alternative types of lenses that similarly satisfy the visual requirements profile, even if no longer ideally, to be specific "Spectacle lens type 1" and "Spectacle lens type 2" (recommendation 3802). On the basis of the assignment rule 3603, there is according to the embodiment also an addition 3900, to be specific the configuration as a second pair of spectacles "Sunglasses" (addition 3901). The addition of a second pair of spectacles is proposed whenever the visual requirements cannot be satisfied sufficiently with one type of spectacle lens and additions. These are especially spectacles for solar protection, working at a PC and special work at close quarters. On the basis of the assignment rule 3604, there is according to the embodiment an addition in the form of the configuration of the ascertainment of the refraction values by taking into consideration aberrations of a higher order "iScription" (addition 3902).

Figure 6A:
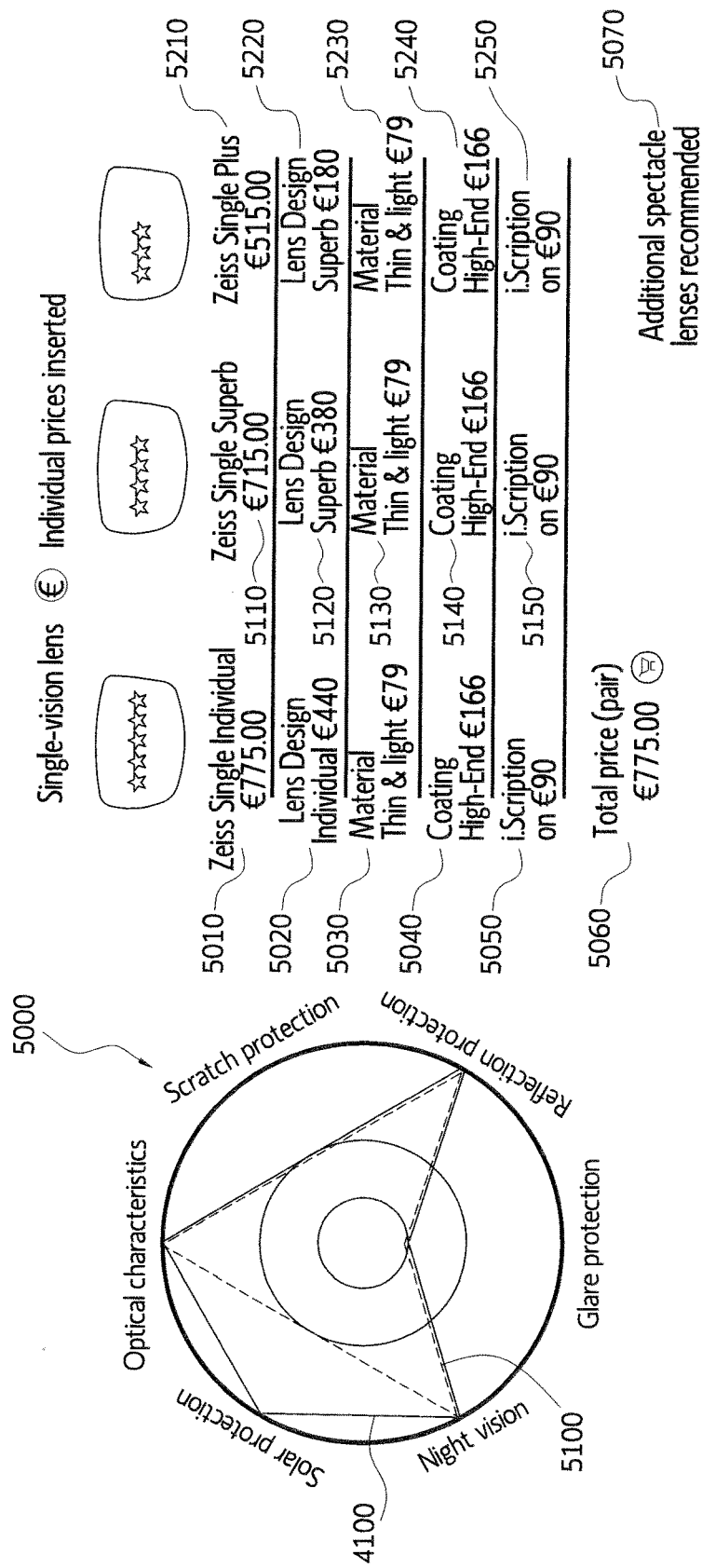
FIGS. 6A and 6B show a graphic representation of a superpositioning of the desired characteristics that are shown in FIG. 5 and the actual characteristics:
A) of a first selected type of spectacle lens; and,
B) of a second selected type of spectacle lens.
Figure 6B:
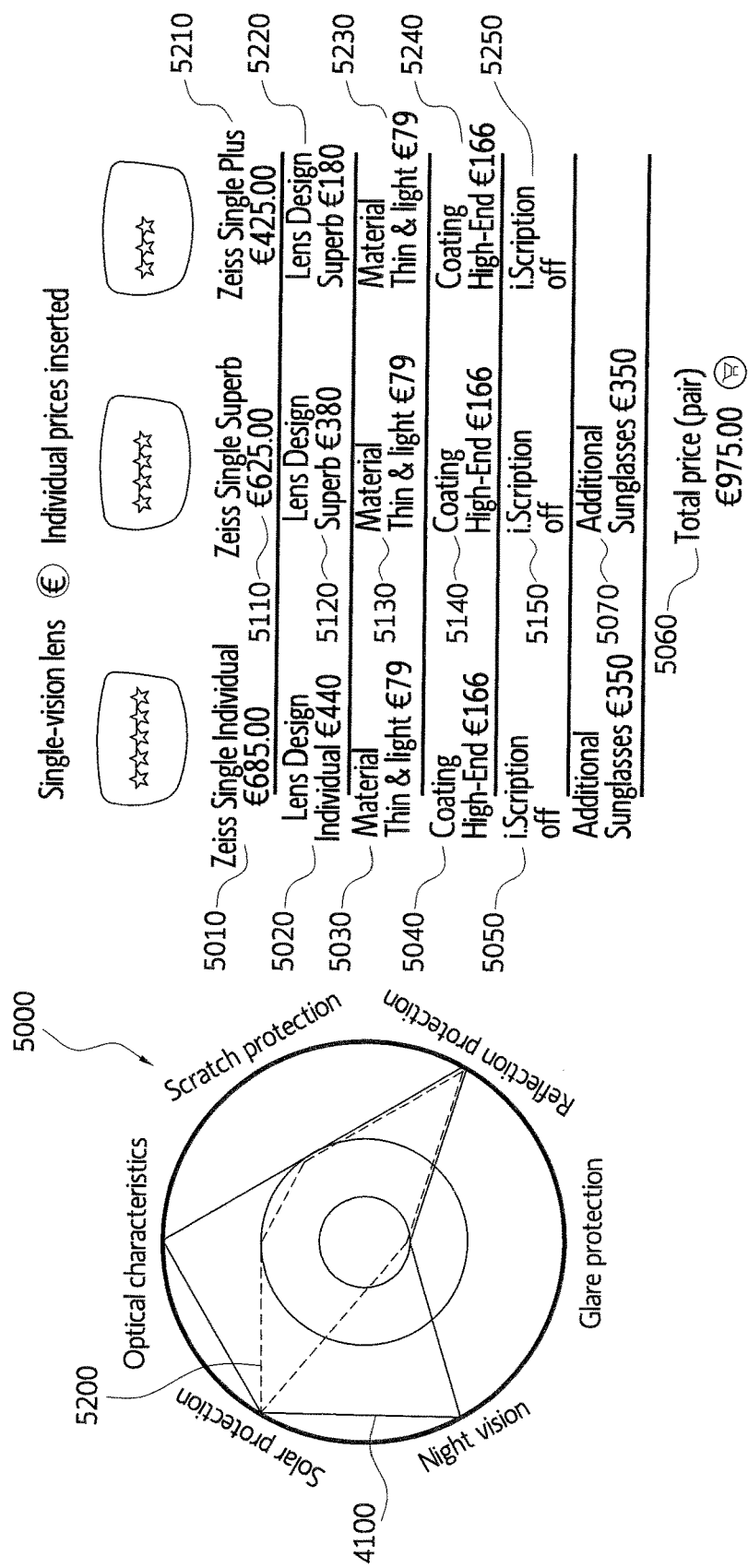

In "Step 6", the types of spectacle lenses ascertained with the aid of the assignment rules described above are displayed on the screen 108, preferably together with corresponding characteristics and features and optional additions. FIG. 6A shows by way of example how such an output 5000 on the screen 108 can look. The left-hand side of FIG. 6A, the individual visual requirements 4100 (profile) here as an outer area of the grid diagram bounded by a solid line, this visual requirements profile is superposed by the actual characteristics 5100 of the type of spectacle lens selected on the right-hand side and the additions thereof (inner area bounded by the dashed line). The right-hand side shows from the range offered by the manufacturer the type of spectacle lens 5010 best matching the requirements, with the variant 5020, material 5030, coating 5040, further features 5050 and price 5060. In addition, in the case of certain visual requirements profiles, one or more additional pairs of spectacles are recommended 5070.

It is also possible here to specify alternative proposals (5110, 5120, 5130, 5140, 5150; 5210, 5220, 5230, 5240, 5250) for the spectacle wearer. Thus, the ophthalmic optician can show the spectacle wearer the degree to which the various spectacle lens solutions satisfy the requirements and compare them. When choosing a proposal (cf. FIG. 6B in comparison with FIG. 6A), it is additionally specified to what degree this spectacle lens solution satisfies the requirements (see the dashed areas for the characteristics 5100, 5200 in FIGS. 6A and 6B).

In addition, it is possible in the case of visual requirements that are mutually exclusive or cannot be satisfied by one spectacle lens solution (for example, driving at night and winter sports) to identify this and propose alternative solutions, such as for example a second pair of spectacles 5070, et cetera.

In the step "Step N" 640, it is provided that an order is placed. Here it is provided that the marked type of spectacle lens and the chosen additions are placed in a basket. From this basket, ordering systems of extremely different types can then retrieve the data and send them to the manufacturer. It is similarly possible in this module to generate an order form and print it out, if the ordering is to be performed by phone or fax.

And in the step "Summary" 642, the user can at any time see an overview of the current status of the individual steps (Steps) and have all the required data available in an overview.

The concept of the method according to the invention and of the apparatus according to the invention for determining a refractive power distribution, adapted to a spectacle wearer, of a progressive spectacle lens is presented below on the basis of two figures.

Figure 7:
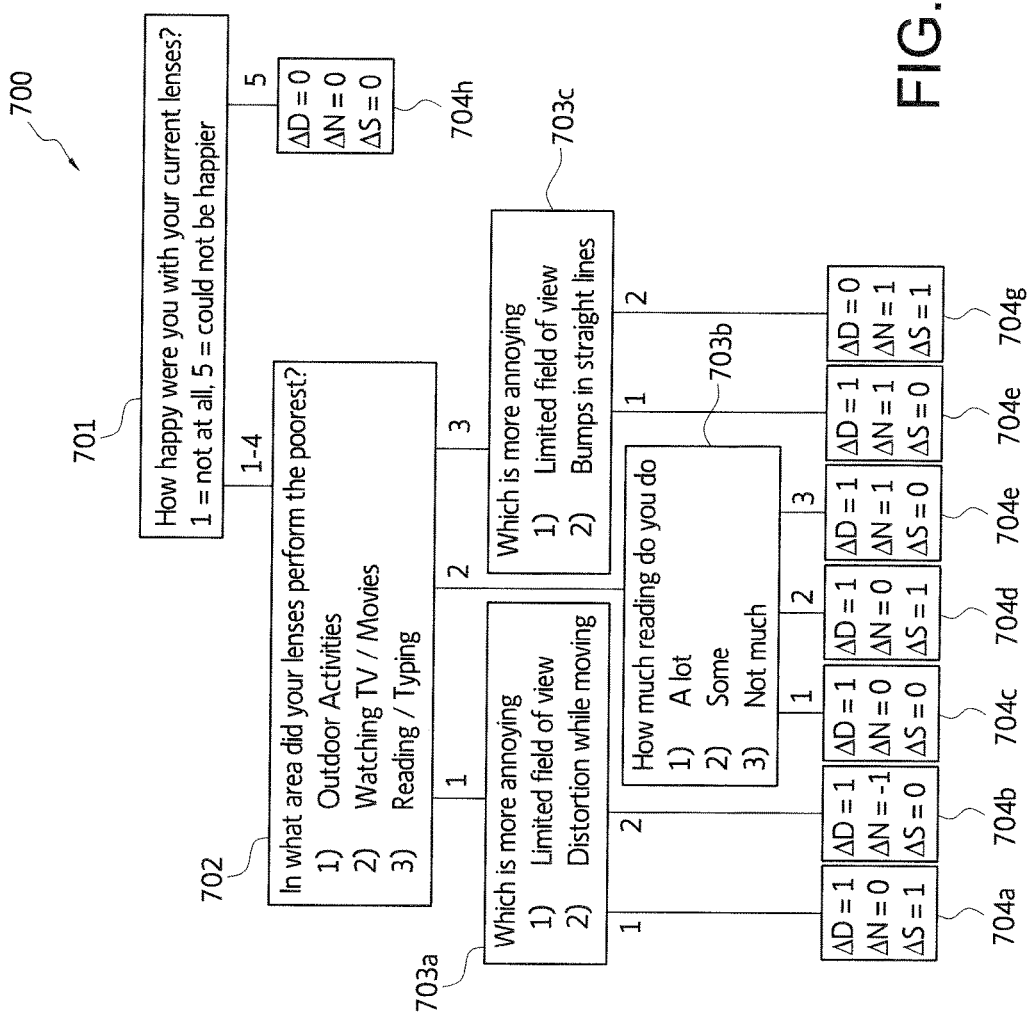
FIG. 7 shows a schematic representation of a simple example that is based on the concept of the method according to the invention for determining a refractive power distribution, adapted to a spectacle wearer, of a progressive spectacle lens; and, FIG. 8 shows a schematic representation for a simple apparatus according to the invention for determining a refractive power distribution, adapted to a spectacle wearer, of a progressive spectacle lens.

FIG. 7 shows a flow diagram of a simple example of a method according to the invention for determining a refractive power distribution, adapted to a spectacle wearer, of a progressive spectacle lens.

The starting situation is a questioning of the customer, for example at the optician's, about the visual impression with his or her progressive spectacles worn in the past, with the aim of providing the customer with new progressive spectacles corresponding better to his or her objective and subjective requirements. In the present embodiment, the questioning of the customer comprises up to three questions, to be specific:

1. How satisfied are you with your present progressive spectacles: completely satisfied, very satisfied, satisfied, not very satisfied, completely unsatisfied?

and in the case where there is not complete satisfaction the question

2. For which of the following activities are your present progressive spectacles least suited: outdoor activities or watching TV/movies or reading/typing?

and, depending on the answer to this question, one of the following questions:

3a. Which is more annoying, a limited field of view or distortion while you are moving?

3b. How much reading do you do, a lot or some or not much?

3c. Which is more annoying, a limited field of view or bumps in straight lines?

The questions are illustrated in FIG. 7 in the form of blocks, to be specific the first question by block 701, the second question by block 702 and questions 3a, 3b and 3c by blocks (703a, 703b, 703c).

The questions are worded in such a way that the respective answer provides information concerning a visual impression of the spectacle wearer with the progressive spectacles worn in the past in the form of an individual visual requirement and i) a corresponding or assigned measure of the quality of the visual impression in connection with the at least one individual visual requirement and/or ii) a corresponding or assigned measure of the frequency of the at least one individual visual requirement. The measure may, for example, be indicated in the form of a numerical measure (such as for example the answer to question 3b: a lot=1, some=2, not much=3) or merely establish a comparative relative reference to some other visual requirement (such as for example the answer to question 1: reading/typing is worse than watching TV/movies and outdoor activities, which can also be expressed, for example, by the following mathematical inequalities: measure of reading/typing<measure of watching TV/movies, measure of reading/typing<measure of outdoor activities). The corresponding numerical measures (1, 2, 3, 4, 5) are indicated in FIG. 7 as output variables for the answers to the questions (701, 702, 703*a*, 703*b*, 703*c*).

Such measures, in particular relative or absolute numerical measures, are accessible to data processing and can be input, for example directly by means of a keyboard, into a data processing system for further processing. It is also possible initially to store these measures in a separate memory and only pass them on to the data processing system for further processing later, for example via a wireless or wire-bound data connection. All of these possibilities for passing on previously ascertained data to the data processing system for further processing that are enumerated above in a non-exhaustive manner are referred to within the present description as provision.

Apart from the information specified above concerning the visual impression of the customer with his or her old progressive spectacles, the optician establishes objectively ascertainable information concerning the refractive power distribution of the old progressive spectacles. This includes in the present embodiment the area dimensions of the extent of the distance-vision part and of the extent of the near-vision part and the value of the gradient of effect at the transition of the near-vision part and the progression corridor. Further measures that may be additionally taken into consideration but have not been taken into consideration in the present embodiment for reasons of clarity are: the value of the gradient of effect at the transition between the distance-vision part and the progression corridor, the value of the near zone inset, the values for the length of and distribution of dioptric affect along the progression corridor and the values of the peripheral astigmatic error distribution outside the distance zone, near zone and progression corridor.

In addition, the optician will establish the current visual characteristics of the spectacle wearer and the current individual needs of the spectacle wearer. The current visual characteristics of the spectacle wearer include the measured values that the optician usually records or acquires when he or she prescribes a customer a new pair of spectacles. These include in particular the current prescription values (sphere, cylinder, prism), the addition, et cetera, as already set out in detail above. The individual requirements include in particular the preferred intended use for the progressive spectacles to be newly designed. Further possible individual needs have already been discussed in detail above. In the present embodiment, it is assumed that the prescription values and the addition have not changed in comparison with the point in time when the "old" spectacles were prescribed. Furthermore, it is assumed that the intended use also remains the same.

Once all of the aforementioned information has been acquired, the method according to the invention can proceed on a computer as follows:
a) The measures of the variables, characterizing the refractive power distribution, of the progressive spectacle lens of the "old" progressive spectacles worn in the past by the spectacle wearer are provided, to be specific
   i) the area value of the distance-vision part (D)
   ii) the area value of the near-vision part (N)
   iii) the value of the gradient of effect at the transition between the near-vision part and the progression corridor (S)

b) the information concerning the current visual impression of the spectacle wearer with the progressive spectacles worn in the past is provided, to be specific for example
   i) the customer is not very satisfied with his or her old progressive spectacles (numerical measure 2 for answer to question 1)
   ii) the customer sees poorly with his or her old spectacles when watching movies. When reading it is better. Leisure activities present no problems (numerical measure 2 for answer to question 2)
   iii) the customer reads a lot (numerical measure 1 for answer to question 3b)
c) the current visual characteristics of the spectacle wearer are provided (unchanged in comparison with previously)
d) the current individual needs of the spectacle wearer are provided (unchanged in comparison with previously)
e) measures of a change
   i) of the area value of the distance-vision part ($\Delta D$)
   ii) of the area value of the near-vision part ($\Delta N$) and
   iii) of the value of the gradient of effect at the transition between the near-vision part and the progression corridor ($\Delta S$)
   are determined, taking into consideration the information provided in step b) concerning the current visual impression of the spectacle wearer with the progressive spectacles worn in the past. If the indications in the block diagram are followed, block 701 leads to the path 1-4 to block 702 and continues from there along path 2 to block 703*b*, and finally by way of path 1 to block 704*c*. Block 704*c* reveals the information concerning the extent of the changes of the provided variables, characterizing the refractive power distribution, of the progressive spectacle lens of the progressive spectacles worn in the past by the spectacle wearer, taking into consideration the provided information concerning the current visual impression of the spectacle wearer with the progressive spectacles worn in the past. According to the measure indicated in block 704*c*, the distance-vision part should be increased by a determined measure, represented by the numerical measure $\Delta D=1$, while the other variables, extent of the near-vision part and gradient at the near-vision part/progression zone transition, should remain unchanged ($\Delta N=0$, $\Delta S00$). Depending on the answers of the spectacle wearer to the questions (701, 702, 703*a*, 703*b*, 703*c*), other measures are obtained for the changes, which are indicated in the blocks (704*a*, 704*b*, 704*c*, 704*d*, 704*e*, 704*f*, 704*g*, 704*h*) in FIG. 7.
f) calculating the refractive power distribution of the progressive spectacle lens for the lens wearer, taking into consideration the provided visual characteristics of the spectacle wearer and the provided individual needs of the spectacle wearer and the determined measure of the change of the at least one of the at least one provided variable, characterizing the refractive power distribution, of the progressive spectacle lens of the progressive spectacles worn in the past by the spectacle wearer.

Figure 8:
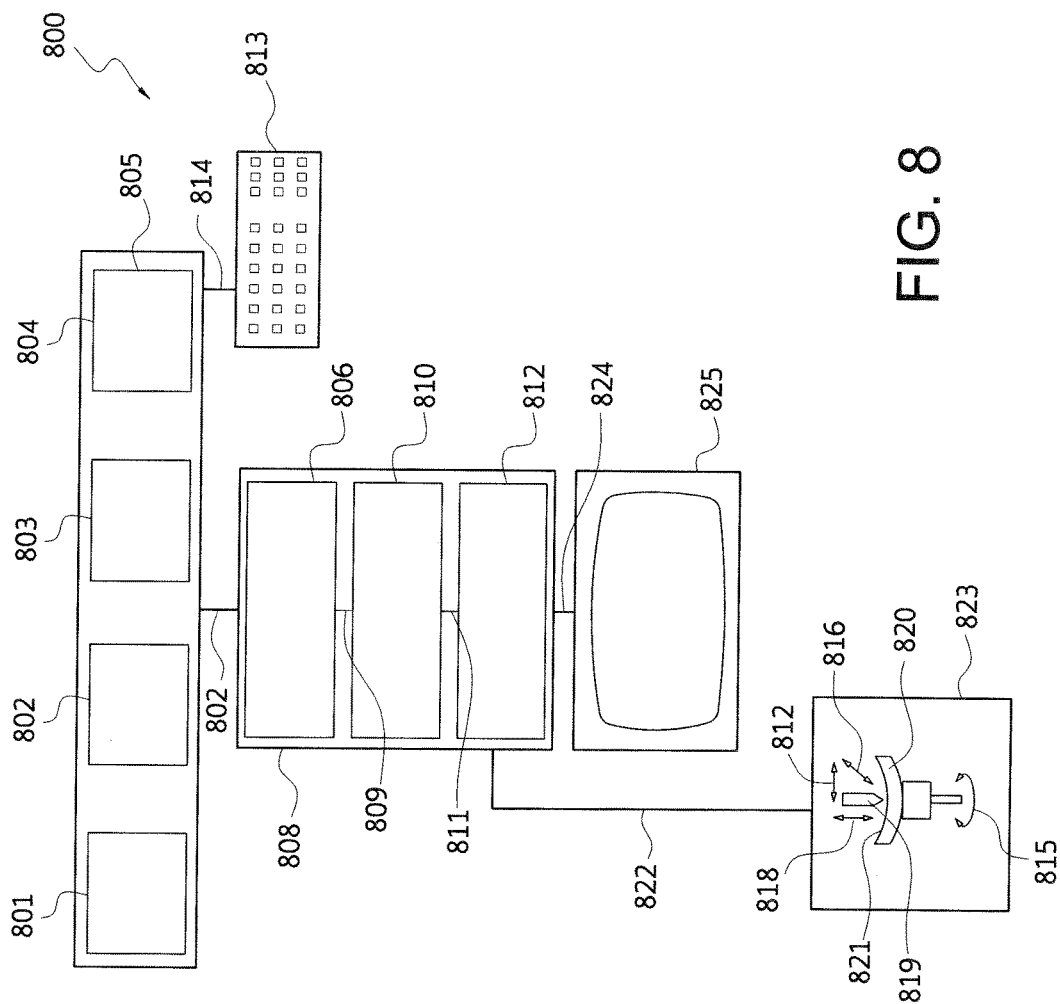

For the sake of completeness, FIG. 8 outlines a simple apparatus according to the invention for determining a refractive power distribution, adapted to a spectacle wearer, of a progressive spectacle lens. This apparatus (for example a data processing system) comprises a first providing device 801, for providing a measure of at least one variable, characterizing the refractive power distribution, of a progressive spectacle lens of progressive spectacles worn in the past by the spectacle wearer, a second providing device 802, for providing current information concerning a visual impression of the spectacle wearer with the progressive spectacles worn in the past, a third providing device 803, for providing current visual characteristics of the spectacle wearer, a fourth providing device 804, for providing current individual needs of the spectacle wearer. In the present embodiment, these are various sectors 801-804 of a memory 805, in which the corresponding information is stored, having previously been input, for example by means of a keyboard 813 connected by way of a data line 814.

This memory 805 is connected by way of a data line 807 to a determining device 806 as a constituent part of a processor 808, for determining a measure of a to-be-desired change for at least one variable, characterizing the refractive power distribution, of the progressive spectacle lens of the progressive spectacles worn in the past by the spectacle wearer, taking into consideration the provided information concerning the current visual impression of the spectacle wearer with the progressive spectacles worn in the past. From this determining device 806 there is a data connection 809 to a calculating device 810, for calculating the refractive power distribution of the progressive spectacle lens for the spectacle wearer, taking into consideration the provided current visual characteristics of the spectacle wearer and the provided current individual needs of the spectacle wearer and the determined measure of the to-be-desired change of the provided measure of the provided at least one variable, characterizing the refractive power distribution, of the progressive spectacle lens of the progressive spectacles worn in the past by the spectacle wearer. Also provided is a calculating device 812, connected by data connection 811, in order to calculate from the refractive power distribution control data for the relative movements (815, 816, 817, 818) of a cutting tool 819 for producing a geometrical shape of at least one area 821 of the progressive spectacle lens 820 to achieve the calculated refractive force distribution of the spectacle lens 820.

In the embodiment presented, the control data may be transferred from the processor 808 to the shaping machine 823 with the cutting tool 819 by way of a data line 822. This data connection 822 may be wire-bound or wireless. The shaping machine 823 may be arranged in the direct vicinity of the processor 808 or be located at another location, possibly even in a different country.

In the present embodiment, the determined measures for a change of the provided measures of the variables, characterizing the refractive power distribution, of the progressive spectacle lens of the progressive spectacles worn in the past by the spectacle wearer and the calculated refractive power distribution may be displayed to the user with the aid of the screen 825, connected to the processor 808 by way of the data line 824.

It is understood that the foregoing description is that of the preferred embodiments of the invention and that various changes and modifications may be made thereto without departing from the spirit and scope of the invention as defined in the appended claims.

What is claimed is:

1. An apparatus for determining a refractive power distribution of a progressive spectacle lens for a spectacle wearer, the progressive lens having a distance portion, a near portion and an intermediate corridor connecting the distance portion and the near portion, the apparatus comprising:

a first providing unit configured to provide a measure for at least one variable characterizing the refractive power distribution of a progressive spectacle lens of a pair of progressive spectacles worn by the spectacle wearer in the past, at least one of the at least one variable originating from a group including: i) dimension of the distance portion (D), ii) the dimension of the near portion (N), iii) gradient of power along a boundary between the distance portion and the intermediate corridor, iv) gradient of power along a boundary between the near portion and the intermediate corridor (S), v) inset, vi) length of and distribution of dioptric power along the intermediate corridor and vii) peripheral astigmatic error distribution outside the distance portion, near portion and intermediate corridor;

a second providing unit configured to provide current information relating to a visual impression of the spectacle wearer with the pair of progressive spectacles worn by the spectacle wearer in the past;

a third providing unit configured to provide current vision characteristics of the spectacle wearer;

a fourth providing unit configured to provide current individual needs of the spectacle wearer;

a determining unit configured to determine a second measure ($\Delta D$, $\Delta N$, $\Delta S$) for a change to be strived for the at least one variable characterizing the refractive power distribution of a progressive spectacle lens of a pair of progressive spectacles worn by the spectacle wearer in the past taking into consideration of the provided information relating to the current visual impression of the spectacle wearer with the pair of progressive spectacles worn by the spectacle wearer in the past; and, a calculating unit configured to calculate the refractive power distribution of the progressive spectacle lens for the spectacle wearer taking into consideration the current vision characteristics of the spectacle wearer and the second measure for a change of the provided measure of the at least one variable characterizing the refractive power distribution of a progressive spectacle lens of a pair of progressive spectacles worn by the spectacle wearer in the past.

2. The apparatus of claim 1 further comprising an outputting unit configured to output the refractive power distribution calculated by said calculating unit.

3. The apparatus of claim 1, wherein the calculating unit is a first calculating unit, the apparatus further comprising a second calculating unit configured to calculate a movement path of a cutting tool for making a geometrical form of at least one surface of the progressive spectacle lens to achieve the refractive power distribution calculated by said first calculating unit.

4. A computer implemented method for determining a refractive power distribution of a progressive spectacle lens for a spectacle wearer, the progressive lens having a distance portion, a near portion and an intermediate corridor connecting the distance portion and the near portion, the computer implemented method comprising the steps of:

providing a measure for at least one variable characterizing the refractive power distribution of a progressive spectacle lens of a pair of progressive spectacles worn by the spectacle wearer in the past, at least one of the at least one variable originating from a group including: i) dimension of the distance portion (D), ii) the dimension of the near portion (N), iii) gradient of power along a boundary between the distance portion and the intermediate corridor, iv) gradient of power along a boundary between the near portion and the intermediate corridor (S), v) inset, vi) length of and distribution of dioptric power along the intermediate corridor and vii) peripheral astigmatic error distribution outside the distance portion, near portion and intermediate corridor;

providing information relating to a current visual impression of the spectacle wearer with the pair of progressive spectacles worn by the spectacle wearer in the past;

providing current vision characteristics of the spectacle wearer;

providing current individual needs of the spectacle wearer;

determining a second measure ($\Delta D$, $\Delta N$, $\Delta S$) for a change of the provided measure of the at least one variable characterizing the refractive power distribution of a progressive spectacle lens of a pair of progressive spectacles worn by the spectacle wearer in the past taking into consideration the provided information relating to the current visual impression of the spectacle wearer with the pair of progressive spectacles worn by the spectacle wearer in the past; and, calculating the refractive power distribution of the progressive spectacle lens for the spectacle wearer taking into consideration the provided current vision characteristics of the spectacle wearer and the determined second measure for a change of the provided measure of the at least one variable characterizing the refractive power distribution of a progressive spectacle lens of a pair of progressive spectacles worn by the spectacle wearer in the past.

5. A method of making a progressive spectacle lens comprising the steps of:

providing a determined refractive power distribution of a progressive spectacle lens for a spectacle wearer, the progressive lens having a distance portion, a near portion and an intermediate corridor connecting the distance portion and the near portion, the refractive power distribution being determined by a computer implemented method including the steps of:

providing a measure for at least one variable characterizing the refractive power distribution of a progressive spectacle lens of a pair of progressive spectacles worn by the spectacle wearer in the past, at least one of the at least one variable originating from a group including: i) dimension of the distance portion (D), ii) the dimension of the near portion (N), iii) gradient of power along a boundary between the distance portion and the intermediate corridor, iv) gradient of power along a boundary between the near portion and the intermediate corridor (S), v) inset, vi) length of and distribution of dioptric power along the intermediate corridor and vii) peripheral astigmatic error distribution outside the distance portion, near portion and intermediate corridor;

providing information relating to a current visual impression of the spectacle wearer with the pair of progressive spectacles worn by the spectacle wearer in the past;

providing current vision characteristics of the spectacle wearer;

providing current individual needs of the spectacle wearer;

determining a second measure ($\Delta D$, $\Delta N$, $\Delta S$) for a change of the provided measure of the at least one variable characterizing the refractive power distribution of a progressive spectacle lens of a pair of progressive spectacles worn by the spectacle wearer in the past taking into consideration the provided information relating to the current visual impression of the spectacle wearer with the pair of progressive spectacles worn by the spectacle wearer in the past;

calculating the refractive power distribution of the progressive spectacle lens for the spectacle wearer taking into consideration the provided current vision characteristics of the spectacle wearer and the determined second measure for a change of the provided measure of the at least one variable characterizing the refractive power distribution of a progressive spectacle lens of a pair of progressive spectacles worn by the spectacle wearer in the past; and, making the progressive spectacle lens with the provided refractive power distribution.

6. A method of making a progressive spectacle lens comprising the steps of:

determining a refractive power distribution of a progressive spectacle lens for a spectacle wearer, the progressive lens having a distance portion, a near portion and an intermediate corridor connecting the distance portion and the near portion, the refractive power distribution being determined by a computer implemented method including the steps of:

providing a measure for at least one variable characterizing the refractive power distribution of a progressive spectacle lens of a pair of progressive spectacles worn by the spectacle wearer in the past, at least one of the at least one variable originating from a group including: i) dimension of the distance portion (D), ii) the dimension of the near portion (N), iii) gradient of power along a boundary between the distance portion and the intermediate corridor, iv) gradient of power along a boundary between the near portion and the intermediate corridor (S), v) inset, vi) length of and distribution of dioptric power along the intermediate corridor and vii) peripheral astigmatic error distribution outside the distance portion, near portion and intermediate corridor;

providing information relating to a current visual impression of the spectacle wearer with the pair of progressive spectacles worn by the spectacle wearer in the past;

providing current vision characteristics of the spectacle wearer;

providing current individual needs of the spectacle wearer;

determining a second measure ($\Delta D$, $\Delta N$, $\Delta S$) for a change of the provided measure of the at least one variable characterizing the refractive power distribution of a progressive spectacle lens of a pair of progressive spectacles worn by the spectacle wearer in the past taking into consideration the provided information relating to the current visual impression of the spectacle wearer with the pair of progressive spectacles worn by the spectacle wearer in the past;

calculating the refractive power distribution of the progressive spectacle lens for the spectacle wearer taking into consideration the provided current vision characteristics of the spectacle wearer and the determined second measure for a change of the provided measure of the at least one variable characterizing the refractive power distribution of a progressive spectacle lens of a pair of progressive spectacles worn by the spectacle wearer in the past; and, making the progressive spectacle lens with the provided refractive power distribution.

7. The method of claim 6 further comprising the steps of:
providing further objective data on the progressive spectacle lens of the progressive spectacles worn in the past by the spectacle wearer; and,
considering the further objective data when calculating the refractive power distribution.

8. The method of claim 7, wherein the further objective data includes at least one of: make, product name, material, coating, working, prescription values, the form and size of frame receiving the spectacle lens, individual parameters and special features of the progressive spectacles worn in the past by the spectacle wearer.

9. The method of claim 6, wherein the information relating to a current visual impression of the spectacle wearer with the pair of progressive spectacles worn by the spectacle wearer in the past includes at least one individual vision requirement and a corresponding measure for the quality of the visual impression in connection with the at least one individual vision requirement.

10. The method of claim 6, wherein the information relating to a current visual impression of the spectacle wearer with the pair of progressive spectacles worn by the spectacle wearer in the past includes at least one measure for the frequency of the at least one individual vision requirement.

11. A computer program comprising program code for, when loaded on a computer, executing a computer implemented method for determining a refractive power distribution of a progressive spectacle lens for a spectacle wearer, the progressive lens having a distance portion, a near portion and an intermediate corridor connecting the distance portion and the near portion, the computer implemented method having the steps of:
providing a measure for at least one variable characterizing the refractive power distribution of a progressive spectacle lens of a pair of progressive spectacles worn by the spectacle wearer in the past, at least one of the at least one variable originating from a group including:
i) dimension of the distance portion (D), ii) the dimension of the near portion (N), iii) gradient of power along a boundary between the distance portion and the intermediate corridor, iv) gradient of power along a boundary between the near portion and the intermediate corridor (S), v) inset, vi) length of and distribution of dioptric power along the intermediate corridor and vii) peripheral astigmatic error distribution outside the distance portion, near portion and intermediate corridor;
providing information relating to a current visual impression of the spectacle wearer with the pair of progressive spectacles worn by the spectacle wearer in the past;
providing current vision characteristics of the spectacle wearer;
providing current individual needs of the spectacle wearer;
determining a second measure ($\Delta D$, $\Delta N$, $\Delta S$) for a change of the provided measure of the at least one variable characterizing the refractive power distribution of a progressive spectacle lens of a pair of progressive spectacles worn by the spectacle wearer in the past taking into consideration the provided information relating to the current visual impression of the spectacle wearer with the pair of progressive spectacles worn by the spectacle wearer in the past; and,
calculating the refractive power distribution of the progressive spectacle lens for the spectacle wearer taking into consideration the provided current vision characteristics of the spectacle wearer and the determined second measure for a change of the provided measure of the at least one variable characterizing the refractive power distribution of a progressive spectacle lens of a pair of progressive spectacles worn by the spectacle wearer in the past.

12. The computer program of claim 11, wherein the computer program is stored on a computer readable storage medium.

\* \* \* \* \*

UNITED STATES PATENT AND TRADEMARK OFFICE
CERTIFICATE OF CORRECTION

PATENT NO. : 10,146,064 B2
APPLICATION NO. : 15/843952
DATED : December 4, 2018
INVENTOR(S) : K. Saur et al.

Page 1 of 1

It is certified that error appears in the above-identified patent and that said Letters Patent is hereby corrected as shown below:

On the Title Page

On page 2:
Under "OTHER PUBLICATIONS", Lines 2, 4 and 12:
Insert -- on which this application is based -- after "PCT/US2013/051529".

On page 2:
Under "OTHER PUBLICATIONS", Line 9:
Insert -- on which this application is based -- after "10 2012 014399.0".

In the Claims

In Column 24:
Line 29: Claim 1, delete "of".

Signed and Sealed this
Twenty-fifth Day of June, 2019

Andrei Iancu
*Director of the United States Patent and Trademark Office*